US009241106B2

(12) United States Patent
Kiuchi

(10) Patent No.: US 9,241,106 B2
(45) Date of Patent: Jan. 19, 2016

(54) IMAGE PROCESSING APPARATUS AND IMAGE PROCESSING METHOD, AND COMPUTER-READABLE STORAGE MEDIUM STORAGE IMAGE PROCESSING PROGRAM

(71) Applicant: OMRON CORPORATION, Kyoto-shi, Kyoto (JP)

(72) Inventor: Yutaka Kiuchi, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 14/058,728

(22) Filed: Oct. 21, 2013

(65) Prior Publication Data
US 2014/0104300 A1    Apr. 17, 2014

Related U.S. Application Data

(62) Division of application No. 12/870,730, filed on Aug. 27, 2010, now abandoned.

(30) Foreign Application Priority Data

Aug. 28, 2009   (JP) ................................ 2009-198408

(51) Int. Cl.
| | |
|---|---|
| H04N 5/222 | (2006.01) |
| H04N 7/18 | (2006.01) |
| G06K 9/00 | (2006.01) |
| H04N 5/232 | (2006.01) |

(Continued)

(52) U.S. Cl.
CPC ....... *H04N 5/23293* (2013.01); *G01N 21/8903* (2013.01); *G06T 11/206* (2013.01); *H04N 5/238* (2013.01); *H04N 5/2351* (2013.01); *H04N 5/23212* (2013.01)

(58) Field of Classification Search
CPC ............ H04N 5/23293; H04N 5/2351; H04N 5/23212
USPC ........................ 348/333.01–333.04, 125–137; 382/141–143, 145–152
See application file for complete search history.

(56) References Cited

U.S. PATENT DOCUMENTS

| | | |
|---|---|---|
| 6,704,012 B1 | 3/2004 | Lefave |
| 6,918,539 B2 | 7/2005 | Nakajima et al. |

(Continued)

FOREIGN PATENT DOCUMENTS

| | | |
|---|---|---|
| JP | 11-004378 | 1/1999 |
| JP | 2000-125179 | 4/2000 |

(Continued)

*Primary Examiner* — Sinh Tran
*Assistant Examiner* — Mark Monk
(74) *Attorney, Agent, or Firm* — Foley & Lardner LLP

(57) ABSTRACT

Provided are an image processing program and an image processing apparatus that support imaging setting in an imaging apparatus. In a focus value display window, temporal change of a focus value (index value) in an input image is outputted. A user operates the imaging apparatus with reference to graph display in the focus value display window to adjust the focus. The focus value displayed in the focus value display window indicates a relatively high value in a "focused" state to a subject such as a work. In the focus value display window, a maximum focus value indicating bar is displayed in association with a focus value indication. The user adjusts the focus state in the imaging apparatus so that the focus value indication "approaches" or "exceeds" this maximum focus value indicating bar as much as possible.

15 Claims, 17 Drawing Sheets

(51) Int. Cl.
*G01N 21/89* (2006.01)
*H04N 5/235* (2006.01)
*H04N 5/238* (2006.01)
*G06T 11/20* (2006.01)

(56) References Cited

U.S. PATENT DOCUMENTS

| | | |
|---|---|---|
| 2003/0059105 A1 | 3/2003 | Hirose et al. |
| 2004/0036792 A1 | 2/2004 | Moriya et al. |
| 2005/0195291 A1* | 9/2005 | Kubo ........................ 348/229.1 |
| 2006/0056733 A1 | 3/2006 | Minakuti et al. |
| 2006/0129353 A1* | 6/2006 | Hattori et al. ............... 348/229.1 |
| 2008/0278618 A1 | 11/2008 | Matsumoto et al. |
| 2009/0174795 A1* | 7/2009 | Kato et al. .................... 348/234 |

FOREIGN PATENT DOCUMENTS

| | | |
|---|---|---|
| JP | 2003-255217 | 10/2003 |
| JP | 2006-085258 | 3/2006 |
| JP | 2008-276115 A | 11/2008 |

* cited by examiner

IMAGE PROCESSING APPARATUS AND IMAGE PROCESSING METHOD, AND COMPUTER-READABLE STORAGE MEDIUM STORAGE IMAGE PROCESSING PROGRAM

CROSS-REFERENCE TO RELATED PATENT APPLICATIONS

Japan Priority Application 2009-198408, filed Aug. 28, 2009 including the specification, drawings, claims and abstract, is incorporated herein by reference in its entirety. This application is a Divisional of U.S. application Ser. No. 12/870,730, filed Aug. 27, 2010, incorporated herein by reference in its entirety.

BACKGROUND OF THE INVENTION

1. Technical Field

The present invention relates to an image processing apparatus to support imaging setting in an imaging apparatus, and an image processing method of the same, and a computer-readable storage medium storing an image processing program.

2. Related Art

In the FA (Factory Automation) field and the like, as an apparatus to optically check the presence or absence of a defect or contamination on an object to be measured such as a work, to optically measure a size thereof and the like, and to optically recognize a character, a graphic and the like on the object to be measured, a so-called visual sensor has been put into practical use. The visual sensor performs various types of image processing to an input image obtained by imaging the object to be measured to thereby output the processing results as described above.

When the visual sensor is set in an actual manufacturing floor or the like, proper image setting needs to be made for the imaging apparatus. As a typical example of the imaging setting, adjustment of a diaphragm amount (luminance), and focus (a focal position) has been known. That is, in order to increase accuracy of the image processing, the adjustment of the diaphragm amount in accordance with an imaging environment (lighting environment), and the adjustment of the focus in accordance with a position relationship between the imaging apparatus and the object to be measured are important.

For example, in Japanese Unexamined Patent Publication No. 2003-255217 (Patent Document 1), there is disclosed a focus adjustment apparatus in which indexes (focus indexes) representing sharpness of two peaks to white and black in a monochrome test pattern are calculated for image data obtained by imaging the white and black test pattern, by which a movement direction on an optical axis of a lens is determined.

Moreover, in Japanese Unexamined Patent Publication No. 2006-85258 (Patent Document 2), there is disclosed an image comparison apparatus and the like in which when a plurality of images photographed by a digital camera are displayed for comparison, evaluation values for use in comparison evaluation (information of high-frequency component, information of an exposure amount, information of a chromaticity value, information of a blurring amount and the like) are displayed.

SUMMARY

However, it is difficult to employ a focus adjustment apparatus using a test pattern as disclosed in Patent Document 1, in the FA field and the like. This is because time and man-hours are needed for arrangement and imaging of the test pattern, and on a line where various types of manufacturing are performed, even if focus is adjusted using a test pattern, the focus may become improper once the object to be measured is replaced.

Moreover, the image comparison apparatus disclosed in Patent Document 2 can only compare the image data after imaging with ease, and it does not provide a function of adjusting the focus of the imaging apparatus, based on a comparison result.

Consequently, the present invention has been devised to solve the problems described above, and an object thereof is to provide an image processing program and an image processing apparatus that support imaging setting in an imaging apparatus.

In accordance with one aspect of the present invention, there is provided an image processing apparatus connected to an imaging apparatus capable of changing imaging setting. The image processing apparatus includes an input unit that takes in an input image acquired by the imaging apparatus, a calculation unit that calculates an index value for evaluating an imaging state in the input image, and an output unit that outputs the index value calculated latest, and the index value calculated before the index value calculated latest.

Preferably, the output unit outputs a history of temporal change of the index value.

More preferably, the image processing apparatus further includes a retention unit that retains a maximum value of the index values respectively calculated for a plurality of input images sequentially taken in by the image input unit. The output unit displays a graph of the index value on a time axis as the history of the temporal change of the index value, and performs display to indicate a position of the maximum value on the graph.

More preferably, the output unit further outputs the input image acquired by the imaging apparatus.

More preferably, a computer is connected to the display apparatus, the output unit displays, on the display apparatus, the maximum value and the input image acquired by the imaging apparatus alongside.

Preferably, the image processing apparatus further includes a determination condition input unit that receives a determination condition concerning the index value, and a determination unit that determines whether or not the index value calculated latest satisfies the determination condition, and the output unit switches an output aspect in accordance with a determination result by the determination unit.

Preferably, the index value is a value indicating an adjustment degree of a diaphragm amount or focus of the imaging apparatus.

In accordance with another aspect of the present invention, there is provided a computer-readable storage medium in which an image processing program to be executed in a computer connected to an imaging apparatus capable of changing imaging setting is stored. The imaging processing program causes the computer to function as an image input unit that takes in an input image acquired by the imaging apparatus, a calculation unit that calculates an index value for evaluating an imaging state in the input image, and an output unit that outputs the index value calculated latest and the index value calculated before the index value calculated latest.

According to the present invention, by supporting the imaging setting in the imaging apparatus by the user, optimal imaging setting can be easily performed.

DETAILED DESCRIPTION

Figure 1:
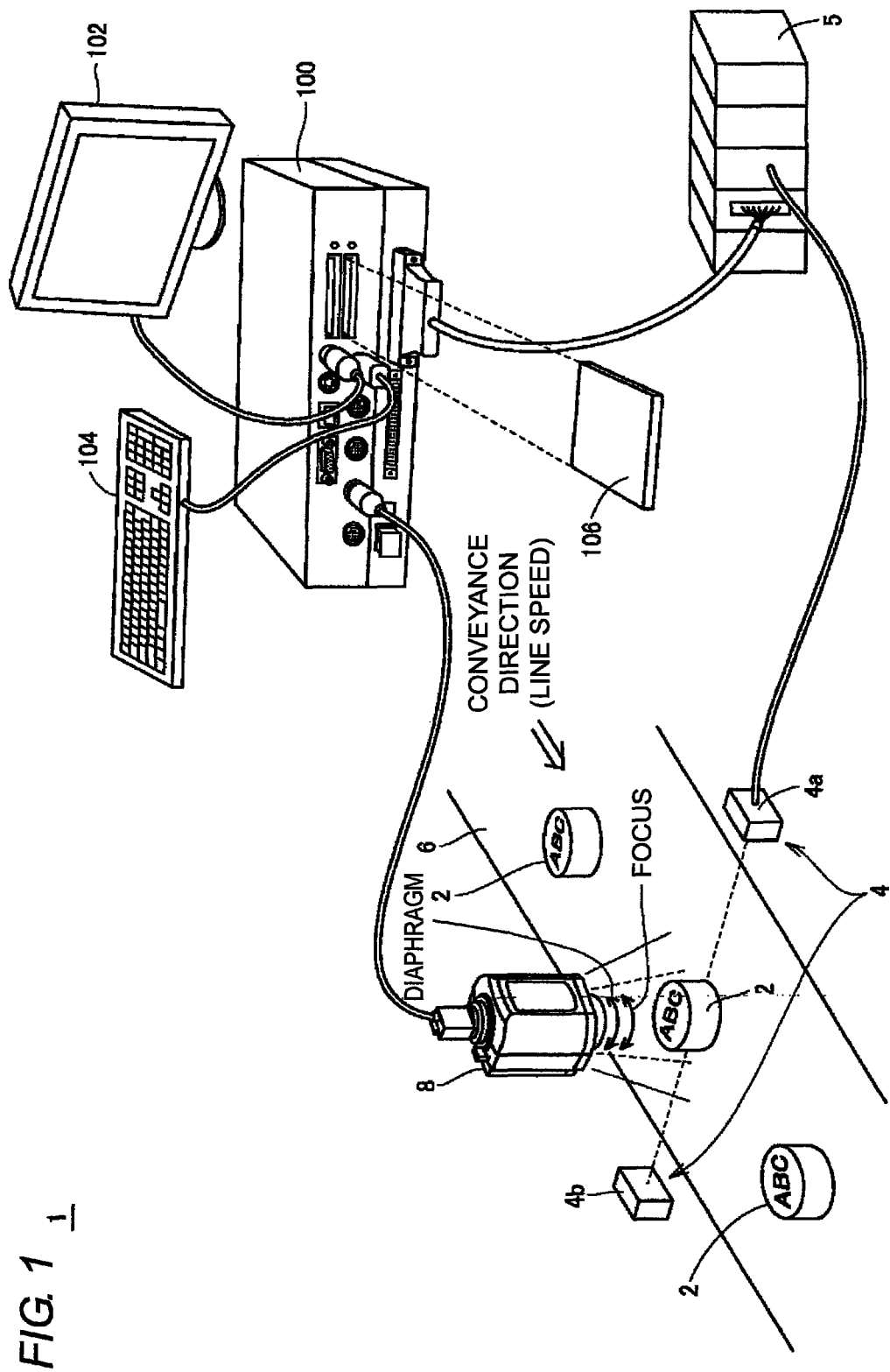
FIG. 1 is a schematic diagram showing an overall configuration of a visual sensor system 1 including an image processing apparatus according to an embodiment of the present invention.

Hereinafter, a preferred embodiment of the present invention will be described with reference to the drawings. The same reference numerals are given to the same or corresponding portions in the figures without repeating their description.

<Overall Apparatus Configuration>

FIG. 1 is a schematic diagram showing an overall configuration of a visual sensor system 1 including an image processing apparatus 100 according to an embodiment of the present invention.

Referring to FIG. 1, the visual sensor system 1 is incorporated in a production line or the like to check the presence or absence of a defect or contamination on an object to be measured 2 (hereinafter, also referred to as a "work 2"), to measure a size thereof and the like, and to recognize a character, a graphic and the like on a surface thereof. As one example, in the present embodiment, the works 2 are conveyed by a conveyance mechanism 6 such as a belt conveyer to sequentially be imaged by an imaging apparatus 8. Image data obtained by the imaging apparatus 8 (hereinafter, also referred to an "input image") is transmitted to the image processing apparatus 100. A lighting mechanism that applies light to the work 2 to be imaged by the imaging apparatus 8 may be further provided.

Arrival of the work 2 at an imaging range of the imaging apparatus 8 is detected by a photoelectric sensor 4 arranged at both ends of the conveyance mechanism 6. Specifically, the photoelectric sensor 4 includes a light receiving part 4a and a floodlight part 4b that are arranged on the same optical axis, and detects the arrival of the work 2 by detecting in the light receiving part 4a that light emitted from the floodlight part 4b is shielded off by the work 2. A detection signal of this photoelectric sensor 4 (hereinafter, also referred to as a "trigger signal") is outputted to a PLC (Programmable Logic Controller) 5.

The PLC 5 receives the trigger signal from the photoelectric sensor 4 or the like, and performs control over the conveyance mechanism 6 itself.

The visual sensor system 1 further includes the image processing apparatus 100, a display 102, and a keyboard 104. The image processing apparatus 100 is connected to the PLC 5, the imaging apparatus 8, the display 102 and the keyboard 104.

The image processing apparatus 100 has a measurement mode in which various types of image processing are executed to the work 2, and an adjustment mode to perform various types of adjustment such as imaging setting. In the measurement mode, the image processing apparatus 100, upon receiving the trigger signal from the photoelectric sensor 4 through the PLC 5, gives an imaging instruction to the imaging apparatus 8. In response to this imaging instruction, an input image obtained by the imaging apparatus 8 imaging the work 2 is transmitted to the image processing apparatus 100. As an alternative processing method, the imaging apparatus 8 is caused to continuously perform the imaging, and in response to the reception of the trigger signal, the image processing apparatus 100 may take in only a necessary input image.

The imaging apparatus 8, as one example, includes, in addition to an optical system such as lenses, an imaging element segmented into a plurality of pixels, such as a CCD (Coupled Charged Device) and a CMOS (Complementary Metal Oxide Semiconductor) sensor. The imaging apparatus 8 has a mechanism capable of changing the imaging setting. As this imaging setting, there are a diaphragm amount (luminance), focus, detection sensitivity (ISO sensitivity), exposure time, shutter speed and the like. In the imaging apparatus 8 according to the present embodiment, as the typical imaging setting, the diaphragm amount (luminance) and the focus can be changed. The present invention can be applied to the imaging apparatus 8 in which at least one item of the items of the imaging setting can be changed.

More specifically, the imaging apparatus 8 includes the optical system having a diaphragm amount adjustment function and a focus adjustment function. That is, to the imaging apparatus 8 are attached a ring for the diaphragm amount adjustment and a ring for the focus adjustment. In the adjustment mode, the image processing apparatus 100 performs processing described later to thereby display an information screen to support the adjustment of the diaphragm amount (luminance) and/or the focus for a worker (user). That is, the user adjusts the imaging apparatus 8, based on index values for evaluating an imaging state in the input image acquired by the imaging apparatus 8, which are displayed on the display 102 or the like, so that the diaphragm amount (luminance) and/or the focus have optimal values.

The image processing apparatus 100 is a computer having a versatile architecture, and executes a program installed in advance to thereby provide various functions described later. When the versatile computer is used, an OS (Operating System) to provide basic functions of the computer may be installed in addition to an application to provide functions according to the present embodiment. In this case, the program according to the present embodiment may call necessary modules in a predetermined order at predetermined timing among program modules provided as a part of the OS, and cause them to execute the processing. That is, the program itself according to the present embodiment does not include the modules, and the processing is executed in cooperation with the OS. For the program according to the present embodiment, the form of not including a part of the modules may be employed.

Furthermore, the program according to the present embodiment may be incorporated in a part of another program to be provided. In this case as well, the program itself does not include the modules included in the other program combined as described above, and the processing is executed in cooperation with the other program. That is, as the program according to the present embodiment, the form of being incorporated in the other program may be employed.

Note that a part or the whole of functions provided by execution of program may be implemented as dedicated hardware circuitry.

Figure 2:
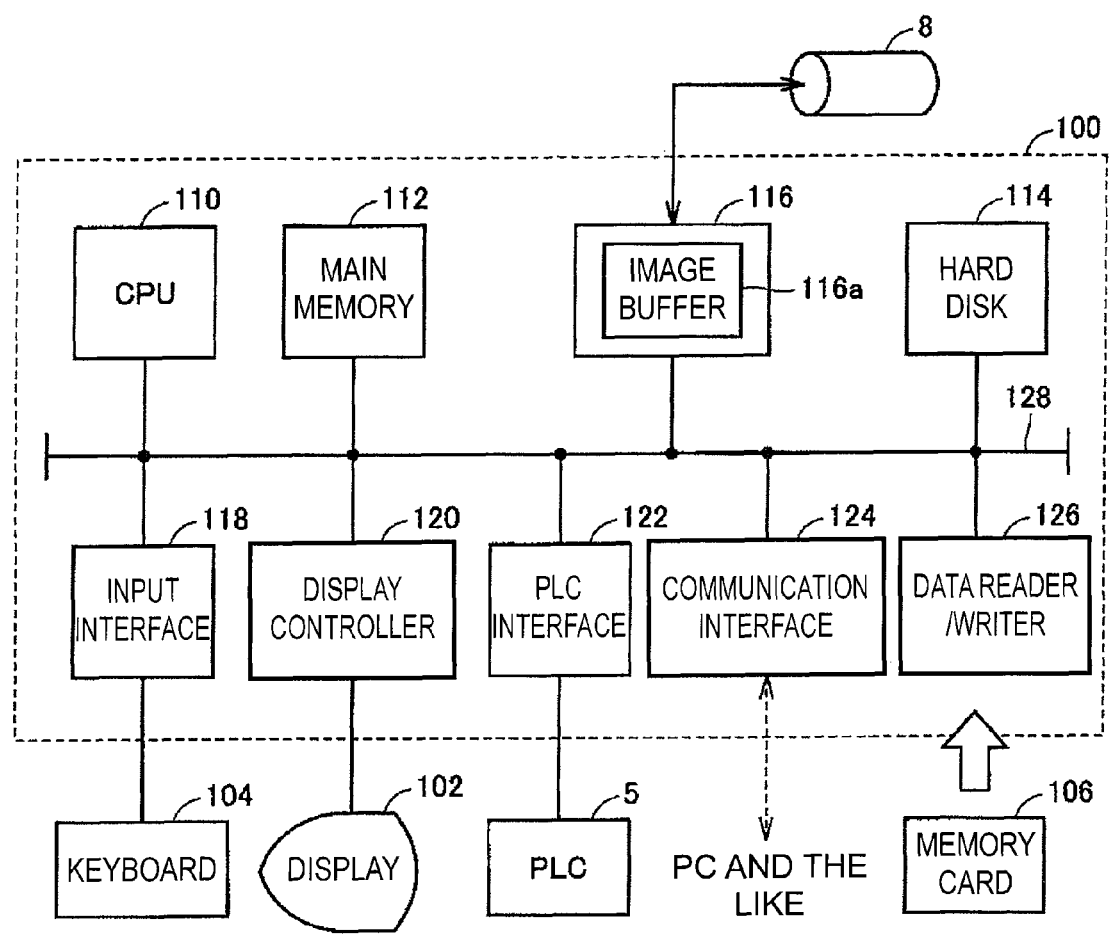
FIG. 2 is a schematic configuration diagram of the image processing apparatus according to the embodiment of the present invention.

FIG. 2 is a schematic configuration diagram of the image processing apparatus 100 according to the embodiment of the present invention. Referring to FIG. 2, the image processing apparatus 100 includes a CPU (Central Processing Unit) 110 as an arithmetic operation processor, a main memory 112 and a hard disk 114 as storage units, and a camera interface 116, an input interface 118, a display controller 120, a PLC interface 122, a communication interface 124, and a data reader/writer 126. These units are connected to one another through a bus 128 so as to enable data communication.

The CPU 110 develops the program (codes) stored in the hard disk 114 to the main memory 112, and executes the same in a predetermined order to conduct various arithmetic operations. The main memory 112 is typically a volatile storage apparatus such as a DRAM (Dynamic Random Access Memory), and retains the input image acquired by the imaging apparatus 8, data indicating a processing result of the input image, work data and the like, in addition to the program read out from the hard disk 114. Moreover, the hard disk 114 is a non-volatile magnetic storage apparatus, and stores various setting values and the like in addition to the program to be executed in the CPU 110. The program installed in this hard disk 114 is distributed in a state stored in the memory card 106 or the like, as described later. In addition to the hard disk 114 or in place of the hard disk 114, a semiconductor storage apparatus such as a flash memory may be employed.

The camera interface 116 mediates data transmission between the CPU 110 and the imaging apparatus 8. More specifically, the camera interface 116 can be connected to the one or more imaging apparatus 8, and includes an image buffer 116a to temporarily accumulate image data from the respective imaging apparatuses 8. When the data of the input image of at least one frame is accumulated in the image buffer 116a, the camera interface 116 transfers the accumulated data to the main memory 112. Moreover, the camera interface 116 gives the imaging instruction to the imaging apparatus 8 in accordance with an internal command issued by the CPU 110.

The input interface 118 mediates data transmission between the CPU 110 and an input apparatus such as the keyboard 104, a mouse and a touch panel. That is, the input interface 118 receives an operation instruction given by the user operating the input apparatus.

The display controller 120 is connected to the display 102 which is a typical example of a display apparatus, and notifies the user of a result of the image processing and the like in the CPU 110.

The PLC interface 122 mediates data transmission between the CPU 110 and the PLC 5. More specifically, the PLC interface 122 transmits, to the CPU 110, information concerning a state of production line controlled by the PLC 5, information concerning the work and the like.

The communication interface 124 mediates data transmission between the CPU 110 and another personal computer, a server apparatus and the like, which are not shown. The communication interface 124 is typically made of the Ethernet (registered trademark), a USB (Universal Serial Bus) and the like. As described later, in place of the form of installing, in the image processing apparatus 100, the program stored in the memory card 106, the program downloaded from a delivery server or the like may be installed in the image processing apparatus 100 through the communication interface 124.

The data reader/writer 126 mediates data transmission between the CPU 110 and the memory card 106 as a storage medium. That is, the program executed in the image processing apparatus 100, and the like are distributed in a state stored in the memory card 106, and the data reader/writer 126 reads the program from this memory card 106. Moreover, in response to an internal instruction of the CPU 110, the data reader/writer 126 writes, in the memory card 106, the input image acquired by the imaging apparatus 8 and/or the processing result and the like in the image processing apparatus 100. The memory card 106 is made of a versatile semiconductor storage apparatus such as a CF (Compact Flash) and an SD (Secure Digital), a magnetic storage medium such as a flexible disk, an optical storage medium such as a CD-ROM (Compact Disk Read Only Memory), or the like.

Moreover, another output apparatus such as a printer may be connected to the image processing apparatus 100 as needed.

<Outline>

The image processing apparatus 100 according to the present embodiment has the measurement mode and the adjustment mode. This measurement mode is a mode in which the work is imaged at proper timing and the preset image processing is sequentially applied to the input image obtained by the imaging. In contrast, the adjustment mode is a mode to set various types of image processing and the like.

The processing described below supports the adjustment of diaphragm amount (luminance) and/or the focus, which is typical examples of the image setting, and is basically provided in the adjustment mode. When the lighting environment changes during measurement (for example, when sunlight is used as illuminating light), these support functions may be enabled to be executed in the measurement mode.

More specifically, the image processing apparatus 100 calculates the index values for evaluating the imaging state in the input image acquired by the imaging of the imaging apparatus 8 to output adjustment support screens including these index values. Since on these index values, right and wrong of the imaging setting of the imaging apparatus is reflected, the user adjusts the image setting of the imaging apparatus 8 so that the displayed index values indicate more optimal values, thereby allowing the user to easily perform the optimal image setting for the imaging apparatus 8.

<1. Luminance Adjustment>

(a. User Interface)

Figure 3:
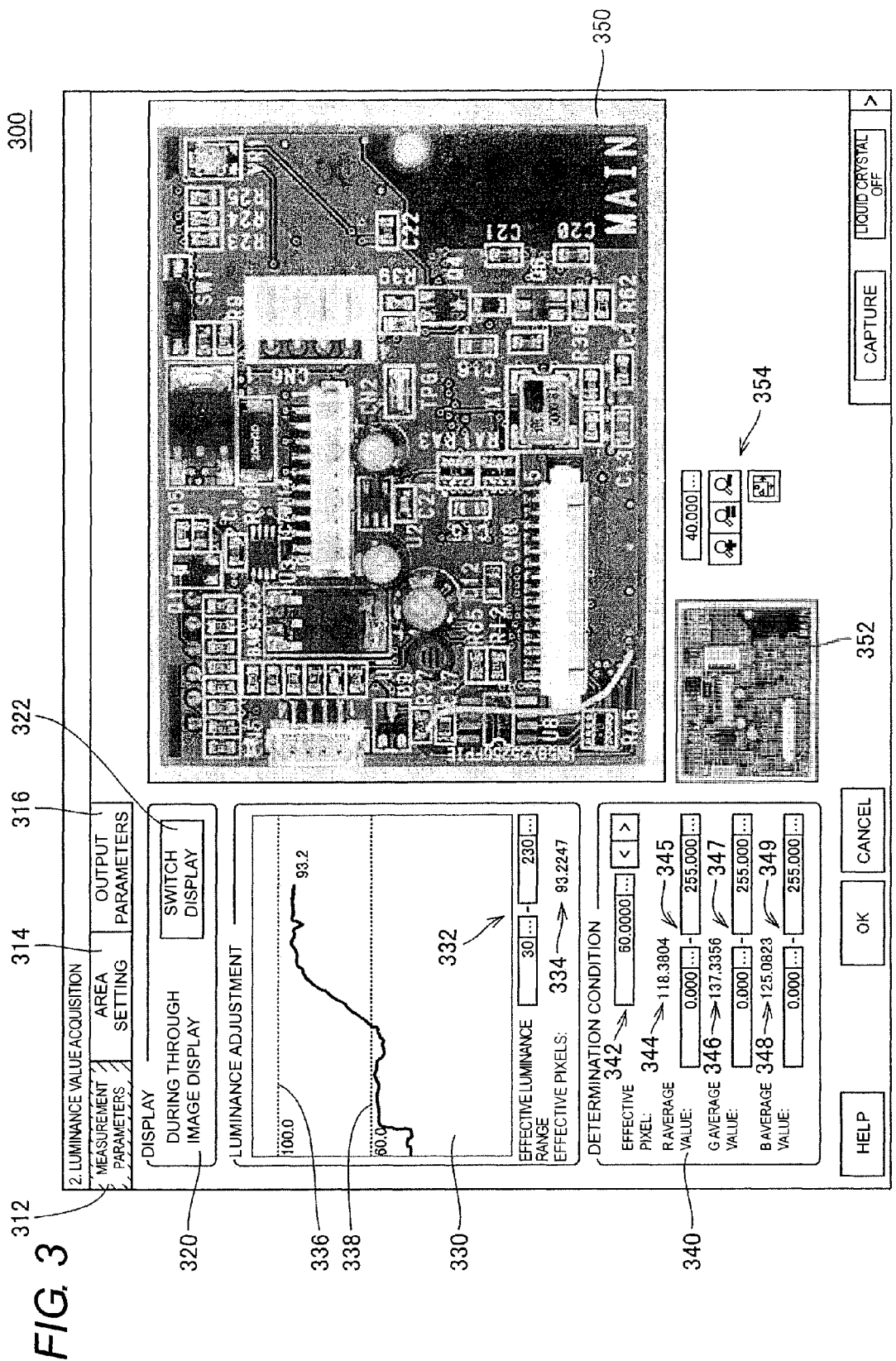
FIG. 3 is a diagram showing one example of a luminance adjustment screen provided by the image processing apparatus according to the embodiment of the present invention.
Figure 4:
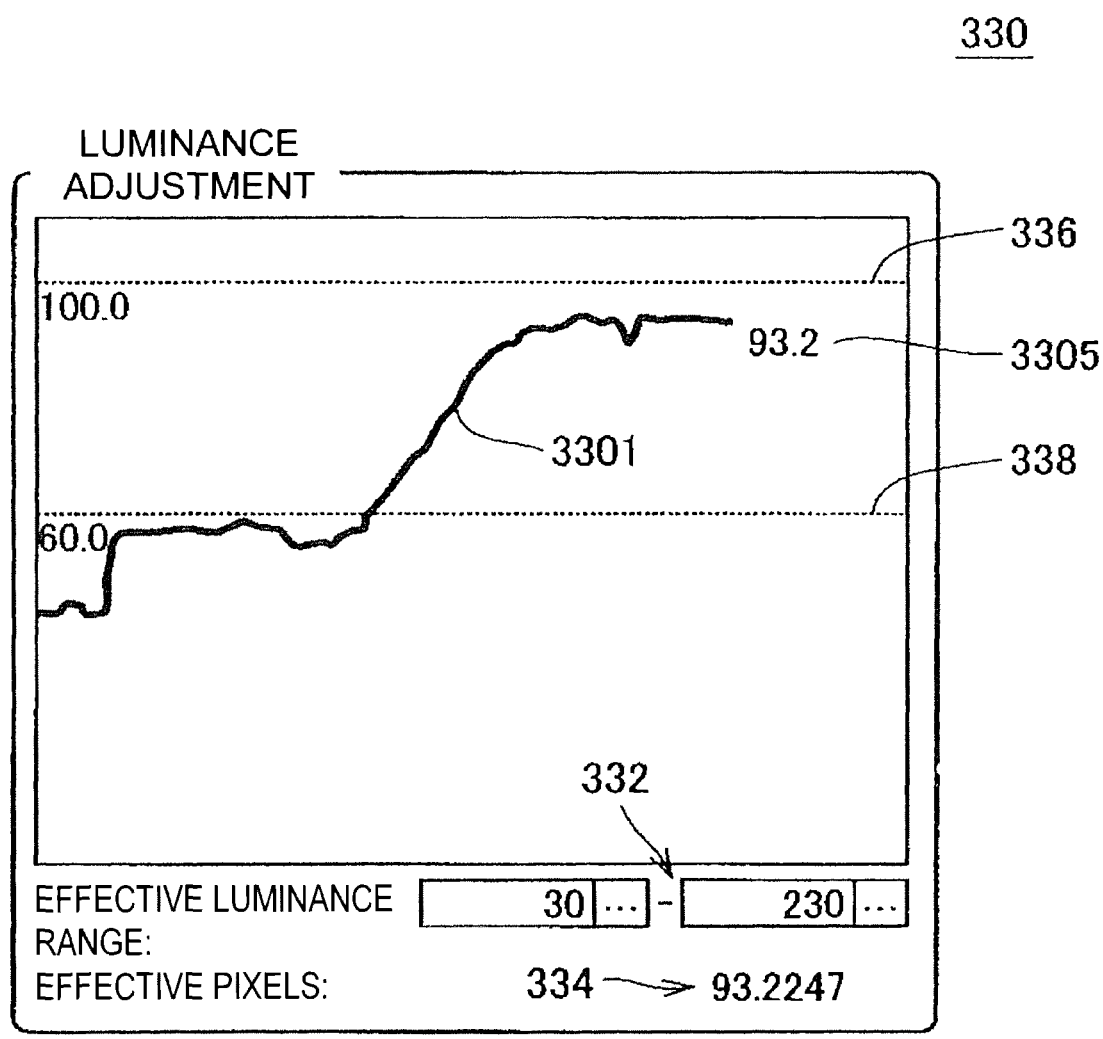
FIG. 4 is an enlarged diagram of a luminance display window shown in FIG. 3.

FIG. 3 is a diagram showing one example of a luminance adjustment screen 300 provided by the image processing apparatus 100 according to the embodiment of the present invention. FIG. 4 is an enlarged diagram of a luminance display window shown in FIG. 3.

Referring to FIG. 3, the image processing apparatus 100 causes the display 102 (FIG. 1) or the like to display a luminance adjustment screen 300.

Referring to FIG. 3, the image processing apparatus 100 according to the present embodiment, in the adjustment mode, provides a screen on which tabs of "measurement parameters", "area setting", and "output parameters" 312, 314, 316 can be selected. On this screen, once the tab 312 of the "measurement parameters" is selected, the luminance adjustment screen 300 as shown in FIG. 3 is provided.

The luminance adjustment screen 300 includes a display-method change window 320, a luminance display window 330, and a determination condition setting window 340, and an image display window 350.

In the image display window 350, the input image acquired by the imaging of the imaging apparatus 8 is displayed. As described later, in accordance with a setting value in the display-method change window 320, an aspect in which images obtained by repeatedly imaging the work with a predetermined period by the imaging apparatus 8 are sequentially displayed (hereinafter, also referred to as a "through mode"), and an aspect in which an image obtained by the imaging apparatus 8 imaging the work at certain timing is statically displayed (hereinafter, also referred to as a "freeze mode") can be selected.

In an overall display window 352, the input image acquired by the imaging of the imaging apparatus 8 is displayed as in the image display window 350. However, in the overall display window 352, the whole of the target input image is displayed independently from a display range in the image display window 350. Furthermore, in accordance with a user operation (scale up or scale down, and the like) to a display control icon group 354, the display range and a display accuracy of the input image displayed in the image display window 350 are changed.

In the display-method change window 320, a display switching button 322 is selectably arranged. When this display switching button 322 is selected, the through mode and the freeze mode are alternately switched. That is, whether or not the input image displayed in the overall display window 352 is sequentially updated is changed. When the freeze mode is selected, it is preferable to stop the update of the luminance display window 330, which will be described later. Moreover, in the display-method change window 320, the mode currently selected is displayed.

In the luminance display window 330, a ratio of the pixels whose luminance is within an effective range in the input image acquired by the imaging of the imaging apparatus 8 is sequentially displayed in a graph. That is, in the luminance display window 330, temporal change of a percentage of the pixels whose luminance is within the effective range (hereinafter, also referred to as an "effective luminance range") to the plurality of pixels making up the input image is displayed in the graph.

The luminance display window 330 includes an effective luminance range control 332, and the user performs an operation to the effective luminance range control 332 to thereby set the effective luminance range. That is, the effective luminance range control 332 receives a condition for evaluating a state of the luminance in the input image acquired by the imaging of the imaging apparatus 8. In an example of FIGS. 3 and 4, as the effective luminance range, an example in which a lower limit value is set to "30", and an upper limit value is set to "230" is shown.

As shown in FIG. 4, a horizontal axis of the graph displayed in the luminance display window 330 indicates time, and a vertical axis indicates the percentage of the number of the pixels having the luminance within the preset effective luminance range (range defined by the lower limit value and the upper limit value set by the effective luminance range control 332) to the total number of pixels included in the input image (hereinafter, the percentage is also referred to as an "effective luminance value"). That is, an effective luminance value corresponds to the index value for evaluating the imaging state in the input image. Specifically, the effective luminance value is calculated in accordance with the following equation (1).

The effective luminance value=(the number of the pixels whose luminance is within the effective luminance range among the pixels included in the input image)/(the total number of the pixels included in the input image)   (1)

In a space defined by the horizontal axis and the vertical axis, an effective luminance value indication 3301 indicating the effective luminance value is graphically displayed sequentially. A logical range of the vertical axis is "0%" to "100%". This effective luminance value is calculated in accordance with the update of the input image to be sequentially updated. While in FIG. 4, the example in which the range of the vertical axis is "0%" to "100%" is shown, a noteworthy range, for example, a range of "50%" to "90%" may be enlarged to be displayed.

More specifically, in the luminance display window 330, the effective luminance value indication 3301 scrolls to the left side in a plane of paper as time passes. That is, a latest result is displayed on the right side in the plane of paper on the horizontal axis. Old data of the effective luminance value indication 3301 that cannot be contained in the luminance display window 330 is not displayed.

The user operates the imaging apparatus 8 with reference to the graph display in the luminance display window 330 to adjust the diaphragm amount. The effective luminance value displayed in this luminance display window 330 indicates a relatively low value when the input image is dark in whole (in the case of underexposure), and when the input image is relatively light in whole (in the case of overexposure). This allows the user to intuitively grasp in which direction (a direction in which incident light is reduced or a direction in which more light is caused to enter) the diaphragm amount of the imaging apparatus 8 is to be adjusted while checking the temporal variation of the effective luminance value indication 3301 in this luminance display window 330. That is, the user adjusts the diaphragm ring of the imaging apparatus 8 so that the effective luminance value indication 3301 in the luminance display window 330 exhibits a higher value.

In this manner, the luminance display window 330 outputs the effective luminance value (index value) calculated latest, and the effective luminance value calculated before the effective luminance value calculated latest.

The luminance display window 330 further includes an effective luminance value indication 334. The effective luminance value indication 334 indicates the effective luminance value at each point. That is, in the effective luminance value indication 334, the substantially same value as a current value 3305 is indicated. Because of limitation of a display area, the number of digits of the current value 3305 may be different from the number of digits of the numerical value indicated by the effective luminance value indication 334.

In the present embodiment, in addition to sequential indication of the effective luminance value, whether or not the calculated effective luminance value satisfies a determination condition is evaluated. This determination condition is arbitrarily set by the user. Examples of the determination condition include a condition that the effective luminance value is within a threshold range, and a condition that an element value of each of the pixels (typically, a density of each color in an RGB color indication system) is within an effective range (hereinafter, also referred to as a "density effective range").

The determination condition (threshold range) concerning the effective luminance value, which is a part of the determination condition, is indicated as an effectiveness upper limit indicating bar 336 and an effectiveness lower limit indicating bar 338 in this luminance display window 330. In the example shown in FIGS. 3 and 4, the effectiveness upper limit indicating bar 336 is displayed in association with a position of "100.0%", and the effectiveness lower limit indicating bar 338 is displayed in association with a position of "60.0%". That is, in the case where only the threshold range (threshold values) concerning the effective luminance value is set as the determination condition, if the effective luminance value indication 3301 is located between the effectiveness upper limit indicating bar 336 and the effectiveness lower limit indicating bar 338, it is determined that the diaphragm amount of the imaging apparatus 8 at the time point satisfies the preset determination condition.

Furthermore, a display aspect of the effective luminance value indication 3301 may be changed between in the case where the effective luminance value at each time point satisfies the preset determination condition, and in the case where it does not satisfy the determination condition. That is, the display is performed so that the user can intuitively grasp whether the imaging is in an "OK state" where the effective luminance value based on the input image acquired at each time point satisfies the determination condition, or in an "NG state" where it does not satisfy the determination condition. In the display, the user can immediately determine whether or not the imaging setting at each time point is proper. The state may be informed not only visually, but also by various warning sounds or the like in combination.

As one example, when the determination condition is satisfied, the effective luminance value indication 3301 is displayed in "green", and when the determination condition is not satisfied, the effective luminance value indication 3301 is displayed in "red". Alternatively, when the determination condition is satisfied, the effective luminance value indication 3301 is "constantly displayed", and when the determination condition is not satisfied, the effective luminance value indication 3301 is "blink-displayed". In this manner, as the change of the display aspect, "display color", "constant display/blink display", "blink period" and the like may be combined as needed so that the user can grasp the state at first glance.

Furthermore, as shown in FIGS. 3 and 4, the current value 3305 may be indicated in association with the effective luminance value indication 3301 ("93.2%" in the example shown in FIGS. 3 and 4). This allows the properness of the luminance adjustment at each time point to be easily grasped.

Referring again to FIG. 3, the determination condition setting widow 340 includes an effective luminance value determination condition control 342, average density indications 344, 346, 348, and density determination condition controls 345, 347, 349.

The effective luminance value determination condition control 342 receives setting of the determination condition for the calculated effective luminance value. That is, the user operates the effective luminance value determination condition control 342, by which the threshold range (threshold values) of the effective luminance value can be arbitrary set. Since the higher effective luminance value is preferable, in the effective luminance value determination condition control 342, an upper limit value of the threshold range is fixed to "100%", and only a lower limit value of the threshold range can be changed. That is, in the example shown in FIGS. 3 and 4, as the threshold range of the effective luminance value, the lower limit value is set to "60", and the upper limit value is set to "100". Either of the upper limit value and the lower limit value of the threshold range may be enabled to be arbitrarily set.

The density determination condition controls 345, 347, 349 receive setting of the determination conditions for an R density value, a G density value, and a B density value, respectively. That is, each of the average density indications 344, 346, 348 receives a threshold range of an average density of the corresponding color (R, G, B). In the present embodiment, the input image obtained by the imaging by the imaging apparatus 8 is data having 8 bits for each of the colors in the RGB color indication system. That is, each of the R density value, G density value and B density value has 256 gradations of 0 to 255. In the example shown in FIG. 3, a case where for any of the density values, a lower limit value of the determination condition (threshold range) is set to "0", and an upper limit value is set to "255" is shown.

Moreover, in the average density indications 344, 346, 348, average values of the R density values, G density values and B density values are indicated. As calculation targets of these average values, all the pixels included in the input image may be included, or only the pixels whose luminance is within the effective luminance range may be included. These average values are compared with the determination condition set in the average density indications 344, 346, 348.

(b. Usage Example)

Figure 5A:
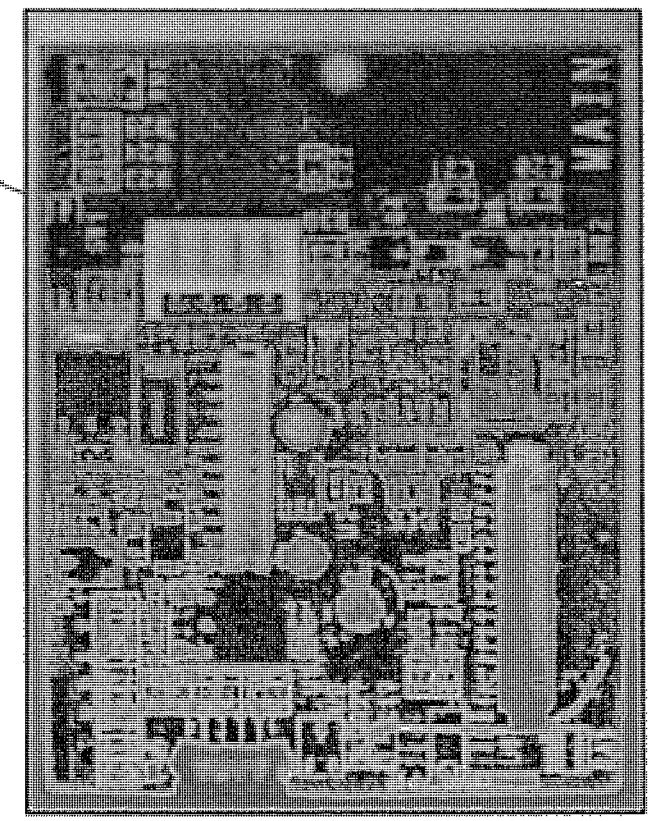
FIGS. 5A, 5B, 5C are diagrams each showing an example of luminance adjustment using the luminance adjustment screen shown in FIG. 3.
Figure 5A:
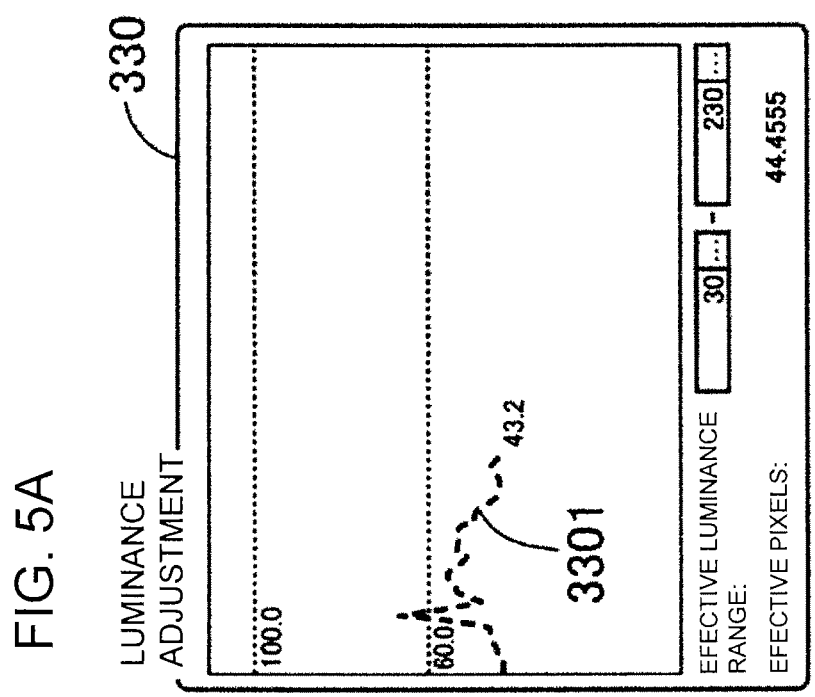
Figure 5B:
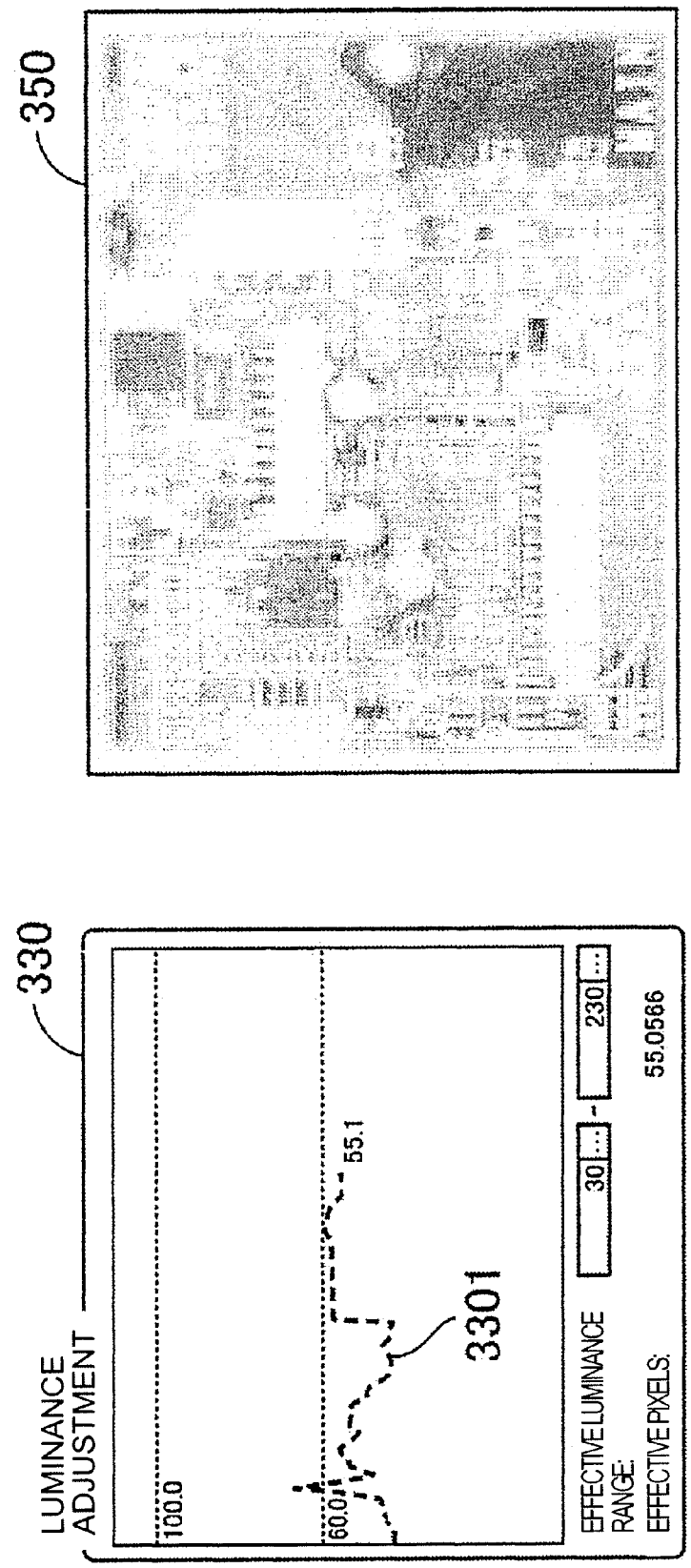
Figure 5C:
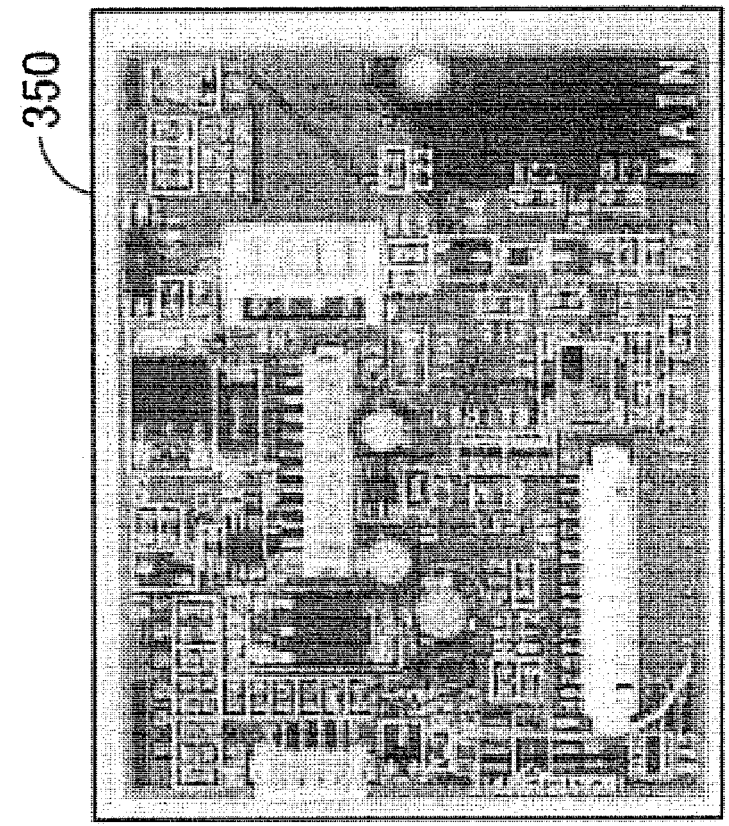
Figure 5C:
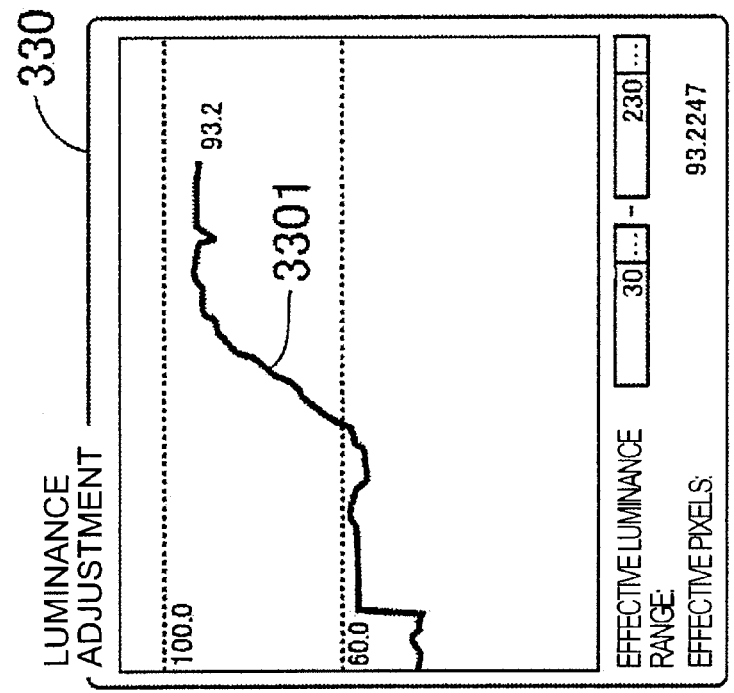

Next, a usage example of the luminance adjustment screen 300 according to the present embodiment is described. FIGS. 5A to 5C are diagrams each showing an example of the luminance adjustment using the luminance adjustment screen 300 shown in FIG. 3. In each of FIGS. 5A to 5C, the luminance display window 330 and the image display window 350 in a certain state of the luminance adjustment screen 300 are displayed in association with each other.

In FIG. 5A, a case where the user has erroneously adjusted the imaging apparatus 8 in the direction in which the diaphragm amount becomes excessive is shown. In this case, the effective luminance value indication 3301 of the luminance display window 330 is found to go down as time passes. That is, the erroneous adjustment gradually decreases the percentage of the number of the pixels included in the effective luminance range. As a result, in the image display window 350, the dark input image in whole is displayed.

On the other hand, in FIG. 5B, a case where the user has erroneously adjusted the imaging apparatus 8 in the direction in which the diaphragm amount becomes too small is shown. In this case as well, the effective luminance value indication 3301 of the luminance display window 330 is found to go down as time passes. That is, the erroneous adjustment gradually decreases the percentage of the number of the pixels included in the effective luminance range. As a result, the image display window 350, the light input image in whole is displayed.

In contrast, in FIG. 5C, a case where the user has adjusted the diaphragm amount of the imaging apparatus 8 is shown. Specifically, the user checks the motion (temporal change) of the effective luminance value indication 3301 while slowly turning the ring for the diaphragm amount adjustment of the imaging apparatus 8, and adjusts the diaphragm amount (and additionally a lighting amount) to that at a point when the effective luminance value reaches a peak. In this case, since with the luminance adjustment by the user, the percentage of the number of the pixels included in the effective luminance range gradually increases, the effective luminance value indication 3301 of the luminance display window 330 is found to go up as time passes. As a result, in the image display window 350, the input image having a proper luminance is displayed. That is, the input image suitable for the image processing with less halation and less black-out can be acquired.

In the luminance display window 330 shown in FIGS. 5A to 5C, in order to indicate that the effective luminance value does not satisfy the determination condition (the NG state), the effective luminance value indication 3301 is displayed by a dashed line, and in order to indicate that the effective luminance value satisfies the determination condition (the OK state), the effective luminance value indication 3301 is displayed by a solid line.

(c. Control Structure)

Next, a control structure to provide the luminance adjustment screen 300 is described.

Figure 6:
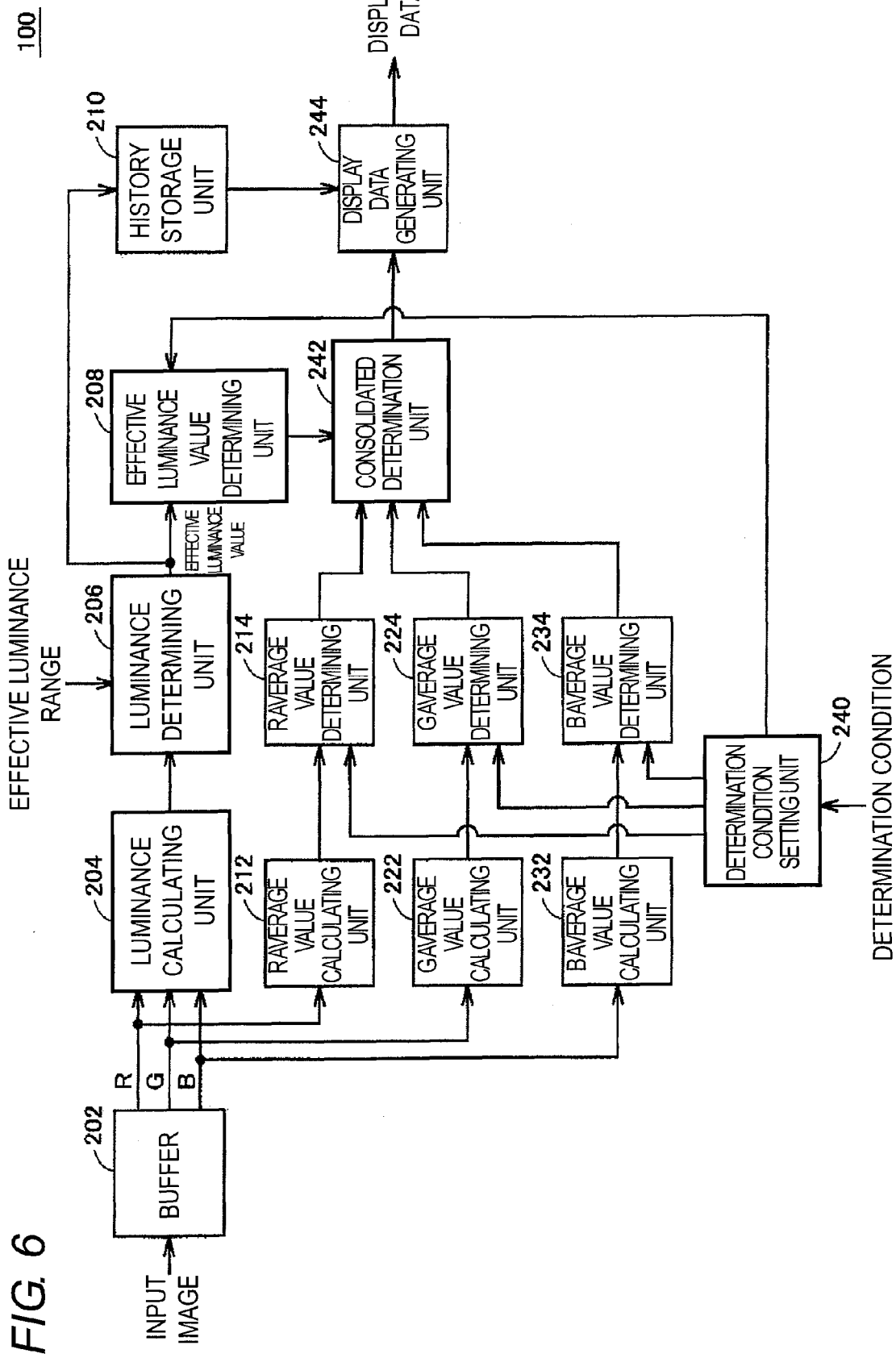
FIG. 6 is a block diagram showing a control structure to provide the luminance adjustment screen according to the embodiment of the present invention.

FIG. 6 is a block diagram showing a control structure to provide the luminance adjustment screen 300 according to the embodiment of the present invention. Respective blocks shown in FIG. 6 are provided by the CPU 110 developing the program (codes) stored in the hard disk 114 to the main memory 112 to execute. The program stored in the hard disk 114 may include a plurality of modules corresponding to the blocks shown in FIG. 6. Alternatively, a part or the whole of the control structure shown in FIG. 6 may be implemented by dedicated hardware and/or wiring circuitry.

Referring to FIG. 6, the image processing apparatus 100, as the control structure, includes a buffer 202, a luminance calculating unit 204, a luminance determining unit 206, an effective luminance value determining unit 208, a history storage unit 210, an R average value calculating unit 212, an R average value determining unit 214, a G average value calculating unit 222, a G average value determining unit 224, a B average value calculating unit 232, a B average value determining unit 234, a determination condition setting unit 240, a consolidated determination unit 242, and a display data generating unit 244.

The buffer 202 temporarily accumulates the input image obtained by the imaging of the imaging apparatus 8. That is, the buffer 202 takes in the input image acquired by the imaging apparatus 8. This input image has a data structure in which the respective pixels are defined by the R density value, the G density value, and the B density value, and the buffer 202 receives access from other sites described later.

The luminance calculating unit 204 calculates the luminance of each of the pixels included in the input image accumulated in the buffer 202. That is, the luminance calculating unit 204 calculates the index value for evaluating the imaging state in the input image. More specifically, if the density values of the respective pixels are Ri, Gi, Bi $\{1 \leq i \leq N\}$, the luminance calculating unit 204 calculates a luminance Li in accordance with the following equation (2).

$$Li = a \times Ri + b \times Gi + c \times Bi \quad (2)$$

where a, b, c are transmission constants.

The luminance calculating unit 204 sequentially outputs the calculated luminance of each of the pixels to the luminance determining unit 206.

The luminance determining unit 206 determines whether or not the luminance is within the preset effective luminance range (see the effective luminance range control 332 of FIG. 3) every time the luminance of each of the pixels of the input image is received from the luminance calculating unit 204. When the luminance determining unit 206 finishes the determination as to all the pixels included in the target input image, it calculates the effective luminance value based on the determination results, and outputs the calculated effective luminance value to the effective luminance value determining unit 208 and the history storage unit 210.

The effective luminance value determining unit 208 determines whether or not the effective luminance value received from the luminance determining unit 206 is within the preset threshold range of the effective luminance value (see the effective luminance value determination condition control 342 of FIG. 3). The effective luminance value determining unit 208 outputs the determination result to the consolidated determination unit 242. That is, the effective luminance value determining unit 208 determines whether or not the effective luminance value (index value) calculated latest satisfies the determination condition.

The history storage unit 210 sequentially stores the effective luminance value received from the luminance determining unit 206. The history storage unit 210 outputs, to the display data generating unit 244, information indicating temporal change of the effective luminance value from the latest effective luminance value to the effective luminance value a predetermined period before.

The R average value calculating unit 212 extracts the R density values of the respective pixels included in the input image accumulated in the buffer 202 to calculate an average value of all the R density values. The R average value calculating unit 212 outputs the calculated average value of the R density values to the R average value determining unit 214.

The R average value determining unit 214 determines whether or not the average value of the R density values received from the R average value calculating unit 212 is within the preset threshold range concerning the average value of the R density values (see the density determination condition control 345 of FIG. 3). The R average value determining unit 214 outputs the determination result to the consolidated determination unit 242.

The G average value calculating unit 222 and the G average value determining unit 224 determine whether or not the average value of the G density values of the input image accumulated in the buffer 202 is within the preset threshold range concerning the average value of the G density values (see the density determination condition control 347 of FIG. 3). Since detailed processing is similar to that of the R average value calculating unit 212 and the R average value determining unit 214, the contents thereof are not repeated.

The B average value calculating unit 232 and the B average value determining unit 234 determine whether or not the average value of the B density values of the input image accumulated in the buffer 202 is within the preset threshold range concerning the average value of the B density values (see the density determination condition control 349 of FIG. 3). Since detailed processing is similar to that of the R average value calculating unit 212 and the R average value determining unit 214, the contents thereof are not repeated.

The determination condition setting unit 240 sets the determination condition set by the user (see the determination condition setting window 340 of FIG. 3) to the corresponding site. That is, the determination condition setting unit 240 receives the determination condition concerning the index value.

The consolidated determination unit 242 determines whether or not the input image accumulated in the buffer 202 satisfies the preset determination condition, based on the respective determination results from the effective luminance value determining unit 208, the R average value determining unit 214, the G average value determining unit 224, and the B average value determining unit 234. The consolidated determination unit 242 outputs the determination result (OK state or NG state) to the display data generating unit 244.

The display data generating unit 244 generates the display data for displaying the luminance adjustment screen 300 shown in FIG. 3. More specifically, the display data generating unit 244 dynamically generates the display contents of the luminance display window 330, based on the information indicating the temporal change of the effective luminance value received from the history storage unit 210, and determines the display aspect, based on the determination result received from the consolidated determination unit 242. Moreover, the display data generating unit 244 also generates data for providing the user interface to set the effective luminance range and the determination condition.

(d. Processing Procedure)

Next, a processing procedure concerning the luminance adjustment is described.

Figure 7:
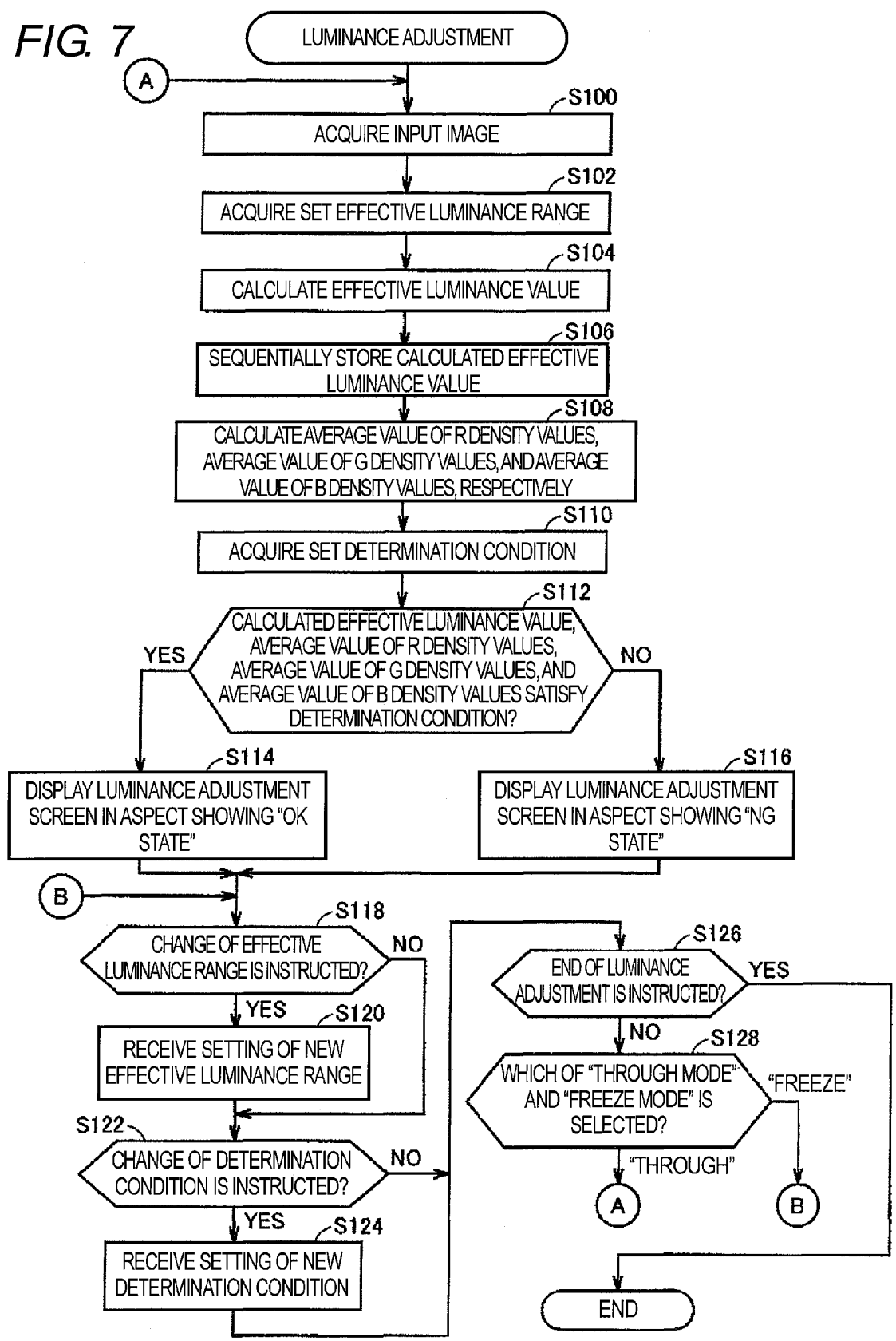
FIG. 7 is a flowchart showing a processing procedure concerning luminance adjustment according to the embodiment of the present invention.

FIG. 7 is a flowchart showing the processing procedure concerning the luminance adjustment according to the embodiment of the present invention. The processing shown in FIG. 7 is started by the user performing a predetermined operation in the adjustment mode.

Referring to FIG. 7, first, the imaging apparatus 8 performs imaging to thereby acquire the input image (step S100). Subsequently, the image processing apparatus 100 (the CPU 110) acquires the set effective luminance range (step S102), and calculates the effective luminance value, based on the whether or not the luminance of each of the pixels included in the input image is within the acquired effective luminance range (step S104). The image processing apparatus 100 (the CPU 110) sequentially stores the calculated effective luminance value (step S106).

Subsequently, the image processing apparatus 100 (the CPU 110) calculates the average value of the R density values, the average value of the G density values, and the average value of the B density values for the input image, respectively (step S108).

Furthermore, the image processing apparatus 100 (the CPU 110) acquires the set determination condition (step S110), and determines whether or not the calculated effective luminance value, the average value of the R density values, the average value of the G density values, and the average value of the B density values satisfy the acquired determination condition (step S112).

If the determination condition is satisfied (if YES in step S112), the image processing apparatus 100 (the CPU 110) displays, on the display 102, the luminance adjustment screen 300 including the effective luminance value indication 3301 indicating the temporal change of the effective luminance value, in the aspect showing the "OK state" (step S114).

In contrast, if the determination condition is not satisfied (if NO in step S112), the image processing apparatus 100 (the CPU 110) displays, on the display 102, the luminance adjustment screen 300 including the effective luminance value indication 3301 indicating the temporal change of the effective luminance value, in the aspect showing the "NG state" (step S116).

Thereafter, the image processing apparatus 100 (the CPU 110) determines whether or not the change of the effective luminance range is instructed (step S118). If the change of the effective luminance range is instructed (if YES in step S118), the image processing apparatus 100 (the CPU 110) receives the setting of the new effective luminance range from the user (step S120). The processing advances to step S122.

If the change of the effective luminance range is not instructed (if NO in step S118), the image processing apparatus 100 (the CPU 110) determines whether or not change of the determination condition is instructed (step S122). If the change of the determination condition is instructed (if YES in step S122), the image processing apparatus 100 (the CPU 110) receives the setting of the new determination condition from the user (step S124). The processing advances to step S126.

If the change of the determination condition is not instructed (if NO in step S122), the image processing apparatus 100 (the CPU 110) determines whether or not end of the luminance adjustment is instructed (step S126). If the end of the luminance adjustment is instructed (if YES in step S126), then the processing ends.

In contrast, if the end of the luminance adjustment is not instructed (if NO in step S126), the image processing apparatus 100 (the CPU 110) determines which of the "through mode" and the "freeze mode" is selected (step S128).

If the "through mode" is selected ("through" in step S128), the processing in step S100 and later is repeated. On the other hand, if the "freeze mode" is selected ("freeze" in step S128), the processing in step S118 and later is repeated. That is, if the freeze mode is selected, the work for taking in a new input image and the calculation processing of the effective luminance value are ceased.

(e. Modification)

While in the embodiment, the configuration in which transition in the percentage of the pixels whose luminance is within the effective luminance range among the pixels included in the input image is displayed is exemplified, a state of the luminance adjustment at each time point may be made clearer from the user friendly standpoint. In a modification described below, a configuration in which a percentage of pixels whose luminance is lower than that in the effective luminance range, and a percentage of pixels whose luminance is higher than that in the effective luminance range among the pixels included in the input image are simultaneously displayed is exemplified. The display allows the user to determine, at first glance, whether the luminance at each time point is in a dark direction in whole, or in a light direction in whole.

In the image processing apparatus according to the present modification, since only the display aspect in the luminance display window included in the luminance adjustment screen 300 is different from that of the image processing apparatus according to the embodiment, detailed descriptions of the other configurations and processing are not repeated.

Figure 8:
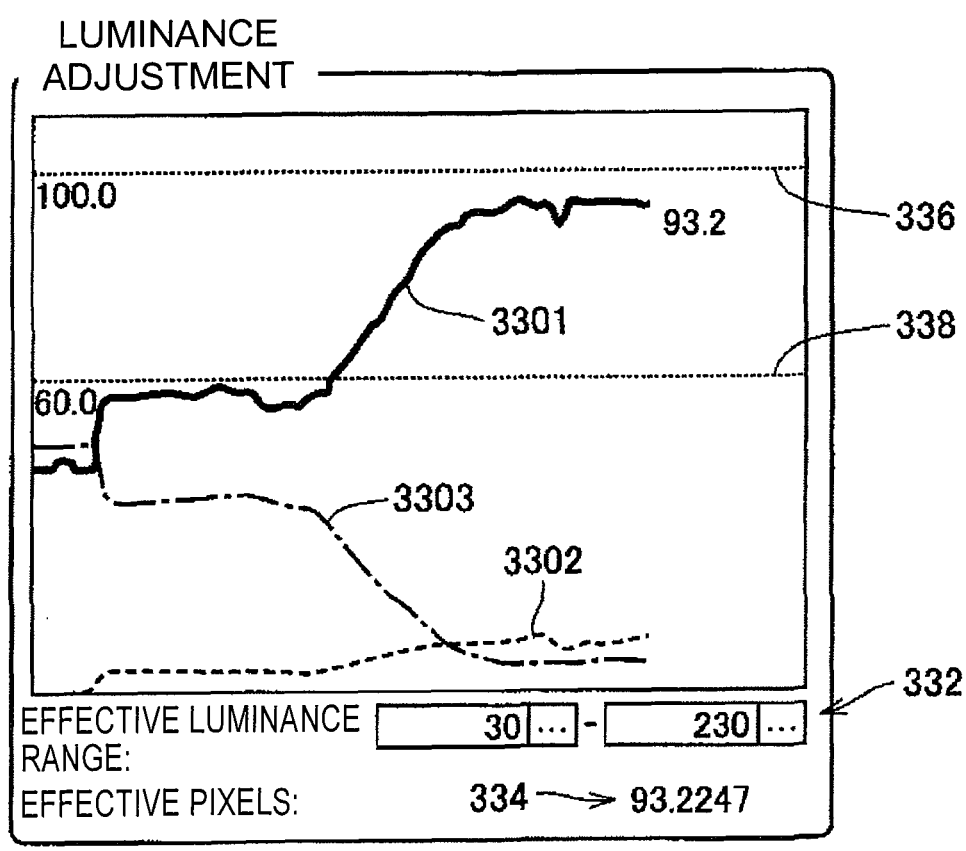
FIG. 8 is a diagram showing a display example of a luminance display window according to a modification of the embodiment of the present invention.

FIG. 8 is a display example of the luminance display window 330A according to the modification of the embodiment of the present invention.

Referring to FIG. 8, the luminance display window 330A according to the present modification includes a first ineffective luminance value indication 3302 and a second ineffective luminance value indication 3303 in addition to the effective luminance value indication 3301 indicating the effective luminance value. The first ineffective luminance value indication 3302 sequentially indicates the percentage of the pixels whose luminance is higher than that in the preset effective luminance range among the pixels included in the input image acquired by the imaging of the imaging apparatus 8 (hereinafter, also referred to as a "first ineffective luminance value"). On the other hand, the second ineffective luminance value indication 3302 sequentially indicates the percentage of the pixels whose luminance is lower than that in the preset effective luminance range among the pixels included in the input image acquired by the imaging of the imaging apparatus 8 (hereinafter, also referred to as a "second ineffective luminance value").

That is, the first ineffective luminance value and the second ineffective luminance value are calculated in accordance with the following equations (3) and (4), respectively.

The first ineffective luminance value=(the number of the pixels whose luminance is higher than that in the effective luminance range among the pixels included in the input image)/(the total number of the pixels included in the input image) (3)

The second ineffective luminance value=(the number of the pixels whose luminance is lower than that in the effective luminance range among the pixels included in the input image)/(the total number of the pixels included in the input image) (4)

Accordingly, at each time point, a sum of the effective luminance value, the first ineffective luminance value and the second ineffective luminance value coincides with "100%".

By referring to the graph display of the first ineffective luminance value indication 3302 and the second ineffective luminance value indication 3303 displayed in the luminance display window 330A shown in FIG. 8, the user can grasp, at first glance, whether the setting of the luminance at each time point is in too dark a state or in too light a state. That is, since if the first ineffective luminance value is relatively high, it indicates that the number of the pixels each having a luminance higher than that in the effective luminance range is relatively large, as a whole, the input image can be determined to be too light. On the other hand, since if the second ineffective luminance value is relatively high, it indicates that the number of the pixels each having a luminance lower than that in the effective luminance range is relatively large, as a whole, the input image can be determined to be too dark.

As described above, employing the luminance display window 330A according to the present modification allows the user to more accurately adjust the diaphragm amount and the like of the imaging apparatus 8.

<2. Focus Adjustment>

(a. User Interface)

Figure 9:
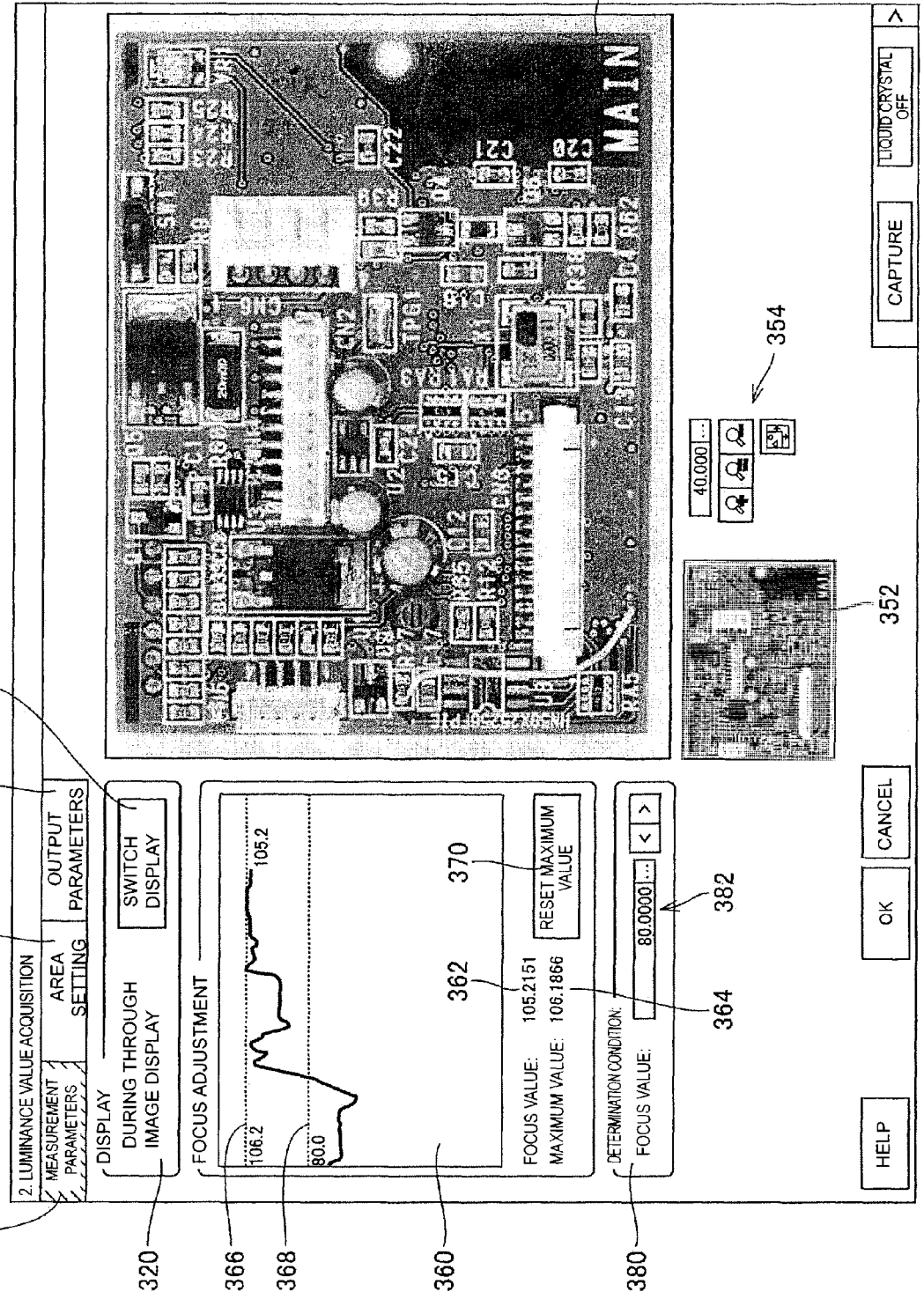
FIG. 9 is a diagram showing one example of a focus adjustment screen provided by the image processing apparatus according to the embodiment of the present invention.
Figure 10:
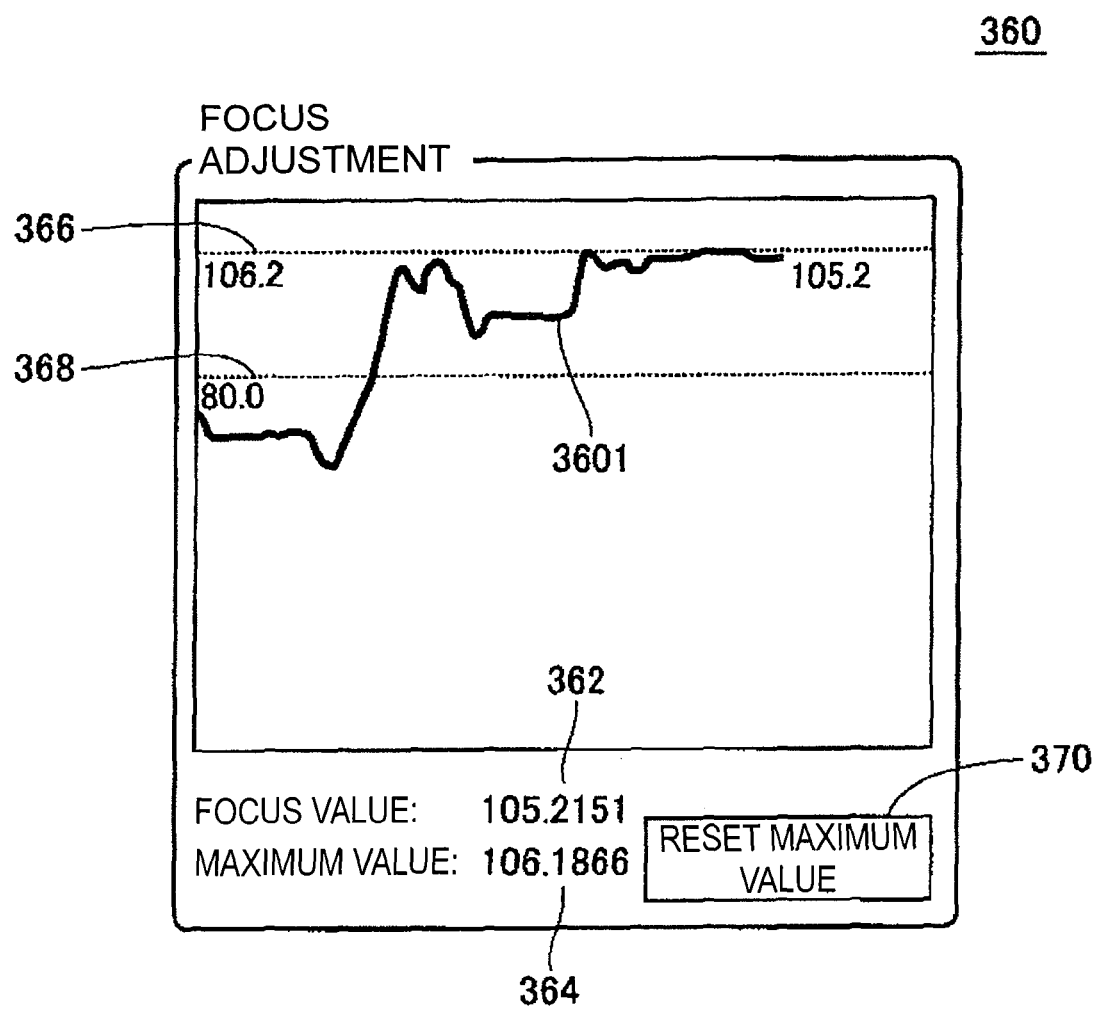
FIG. 10 is an enlarged diagram of a focus value display window shown in FIG. 9.

FIG. 9 is a diagram showing one example of a focus adjustment screen 302 provided by the image processing apparatus 100 according to the embodiment of the present invention. FIG. 10 is an enlarged diagram of a focus value display window shown in FIG. 9.

Referring to FIG. 9, the image processing apparatus 100 causes the display 102 (FIG. 1) or the like to display the focus adjustment screen 302. This focus adjustment screen 302 is provided by selecting the tab 312 of the "measurement parameters".

The focus adjustment screen 302 includes the display-method change window 320, a focus value display window 360, a determination condition setting window 380, and the image display window 350. Since among these windows, the display-method change window 320 and the image display window 350 are similar to the display-method change window 320 and the image display window 350 in the luminance adjustment screen 300 shown in FIG. 3, detailed descriptions thereof are not repeated.

In the focus value display window 360, a focus value in the input image acquired by the imaging of the imaging apparatus 8 is sequentially displayed in a graph. This focus value indicates a degree of whether or not the imaging apparatus 8 comes into focus to a subject such as the work. That is, the focus value corresponds to an index value for evaluating the imaging state in the input image. This focus value has a correlationship with an occurrence amount of edges in the input image. Consequently, in the present embodiment, the focus value is calculated based on color deviation included in the input image. As one example, the focus value is calculated in accordance with the following equation (5).

$$\text{The focus value} = \sqrt{\sum_{C=R,G,B} \{ave(C^2) - ave(C)^2\}} \quad (5)$$

where ave(C) is an average value of density values of a color C of the pixels included in the input image, and ave($C^2$) is a square average value of the density values of the color C of the pixels included in the input image.

As shown in FIG. 10, a horizontal axis of a graph displayed in the focus value display window 360 indicates time, and a vertical axis indicates the focus value concerning the input image. In a space defined by these horizontal axis and vertical axis, a focus value indication 3601 indicating the focus value is plotted sequentially. That is, in the focus value display window 360, temporal change of the focus value (the index value) in the input image is outputted. In other words, as the temporal change of the focus value (index value), the graph of the focus value is displayed on the time axis.

As expressed by the above equation (5), since the focus value employed in the focus adjustment screen 302 according to the present embodiment is a color deviation in the input image, a logical range of the vertical axis varies in accordance with the ranges of the density values of the respective colors. Thus, in accordance with a maximum value of the focus value calculated sequentially, or the like, a display range in the focus value display window 360 is dynamically changed.

In the focus value display window 360, the focus value indication 3601 scrolls to the left side in a plane of paper as time passes. That is, a latest result is displayed on the right side in the plane of paper on the horizontal axis. Old data of the focus value indication 3601 that cannot be contained in the focus value display window 360 is not displayed.

The user operates the imaging apparatus 8 with reference to the graph display in the focus value display window 360 to adjust the focus. The focus value displayed in this focus value display window 360 exhibits a relatively high value in a "focused" state to a subject such as the work. This allows the user to intuitively grasp in which direction (a direction in which a focal position is moved to the farther side or a direction in which the focal position is moved to the closer side) the focus of the imaging apparatus 8 is to be adjusted while checking the temporal change of the focus value indication 3601 in this focus value display window 360. That is, the user adjusts the zoom ring of the imaging apparatus 8 so that the focus value indication 3601 in the focus value display window 360 exhibits a high value.

In the focus value display window 360, a maximum focus value indicating bar 366 is displayed in association with the focus value indication 3601. This maximum focus value indicating bar 366 indicates the highest focus value (maximum focus value) of the calculated results of the past focus values. In the example of FIGS. 9 and 10, the maximum focus value indicating bar 366 indicates "106.2", and the user adjusts a focus state in the imaging apparatus 8 so that the focus value indication 3601 "approaches" or "exceeds" this maximum focus value indicating bar 366 as much as possible.

In this manner, the focus value display window 360 outputs the focus value (index value) calculated latest, and the focus value calculated before the focus value calculated latest (preferably, the maximum focus value). The graph as the temporal change of the focus value is displayed in association with this maximum focus value. Moreover, the maximum focus value indicating bar 366 indicates a position of the maximum focus value on this graph of the focus value.

The focus value display window 360 further includes a maximum value indication 364 and a reset button 370. The maximum value indication 364 numerically indicates the highest focus value in the past, which is indicated by the maximum focus value indicating bar 366. A current value indication 362 indicating the focus value at each time point is arranged along with the maximum value indication 364. That is, in the current value indication 362, the substantially same value as that of the focus value indication 3601 is indicated. However, because of limitation of a display area, the number of digits of the focus value indication 3601 may be different from the number of digits of the numerical value indicated by the current value indication 362.

This highest focus value in the past can be reset by the user pressing the reset button 370. This reset button 370 is used when a focus value different from that in a normal state is recorded in the case where the work as the subject is exchanged, by some causes (for example, improper acquisition of the input image and the like) or the like.

In the present embodiment, in addition to the sequential indication of the focus value, whether or not the calculated focus value satisfies a determination condition is evaluated. This determination condition is arbitrarily set by the user. An example of the determination condition includes a condition that the focus value is higher that a certain threshold value. This determination condition (threshold value) is displayed as a determination lower limit value indicating bar 368 in association with the focus value indication 3601 of the focus value display window 360. In the example shown in FIGS. 9 and 10, the determination lower limit value indicating bar 368 is displayed in association with a position of "80.0%". That is, when the focus value indication 3601 is located above the determination lower limit value indicating bar 368, it is determined that the focus value of the imaging apparatus 8 at the time point satisfies the preset determination condition.

Furthermore, a display aspect of the focus value indication 3601 may be changed between in the case where the focus value at each time point satisfies the preset determination condition, and in the case where it does not satisfy the determination condition. That is, the display is performed so that the user can intuitively grasp whether the imaging is in an "OK state" where the focus value based on the input image acquired at each time point satisfies the determination condition, or in an "NG state" where it does not satisfy the determination condition. The display allows the user to immediately determine whether or not the imaging setting at each time point is proper. The state may be informed not only visually, but also by various warning sounds or the like in combination.

As one example, when the determination condition is satisfied, the focus value indication 3601 is displayed in "green", and when the determination condition is not satisfied, the focus value indication 3601 is displayed in "red". Alternatively, when the determination condition is satisfied, the focus value indication 3601 is "constantly displayed", and when the determination condition is not satisfied, the focus value indication 3601 is "blink-displayed". In this manner, as the change contents of the display aspect, "display color", "constant display/blink display", "blink period" and the like may be combined as needed so that the user can grasp the state at first glance.

The determination condition is set by a focus value determination condition control 382 included in the determination condition setting window 380. That is, the user operates the focus value determination condition control 382 to thereby set the threshold value (threshold range) to reverse so that the focus value becomes effective.

(b. Usage Example)

Figure 11A:
FIGS. 11A, 11B, 11C are diagrams each showing an example of the focus adjustment using the focus adjustment screen shown in FIG. 9.
Figure 11A:
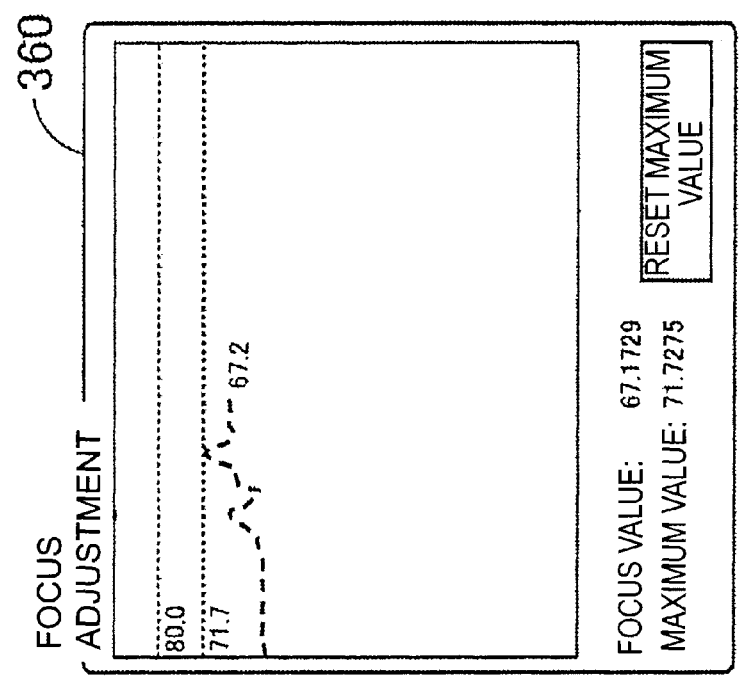
Figure 11B:
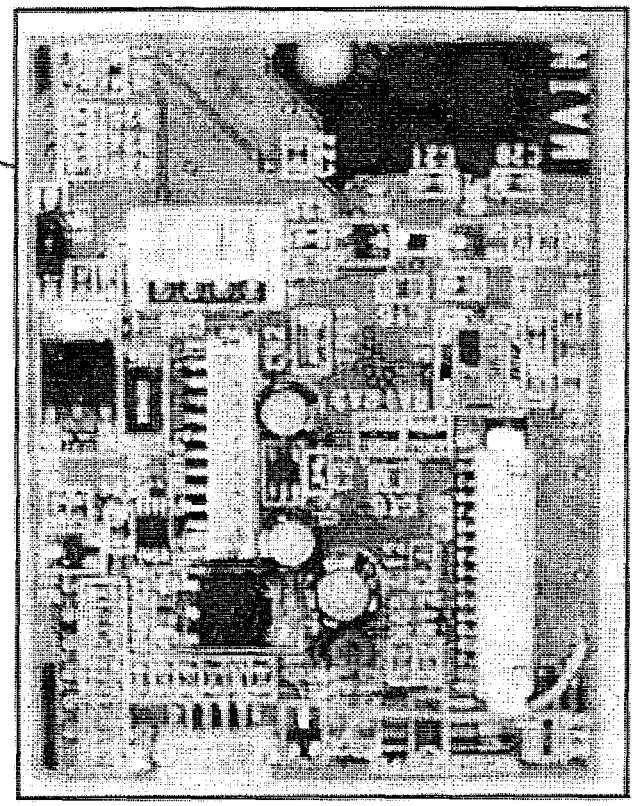
Figure 11B:
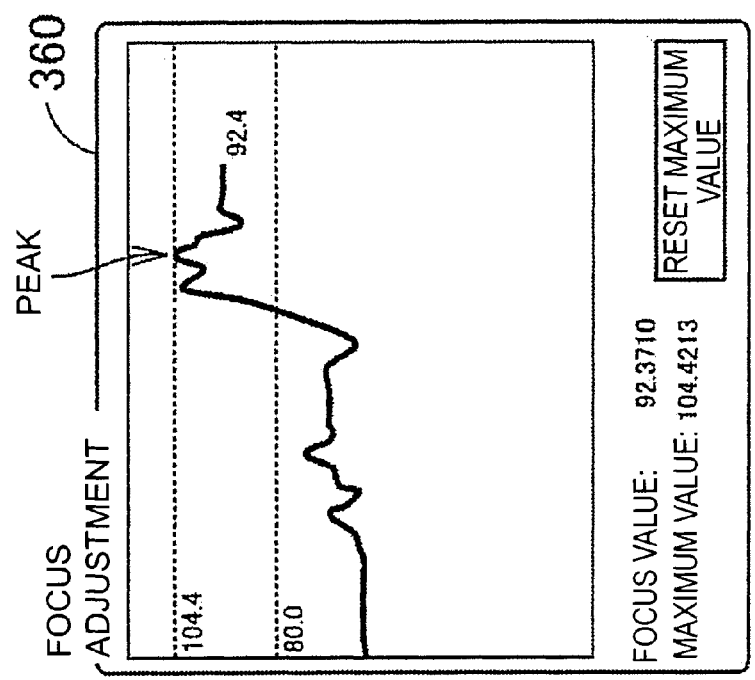
Figure 11C:
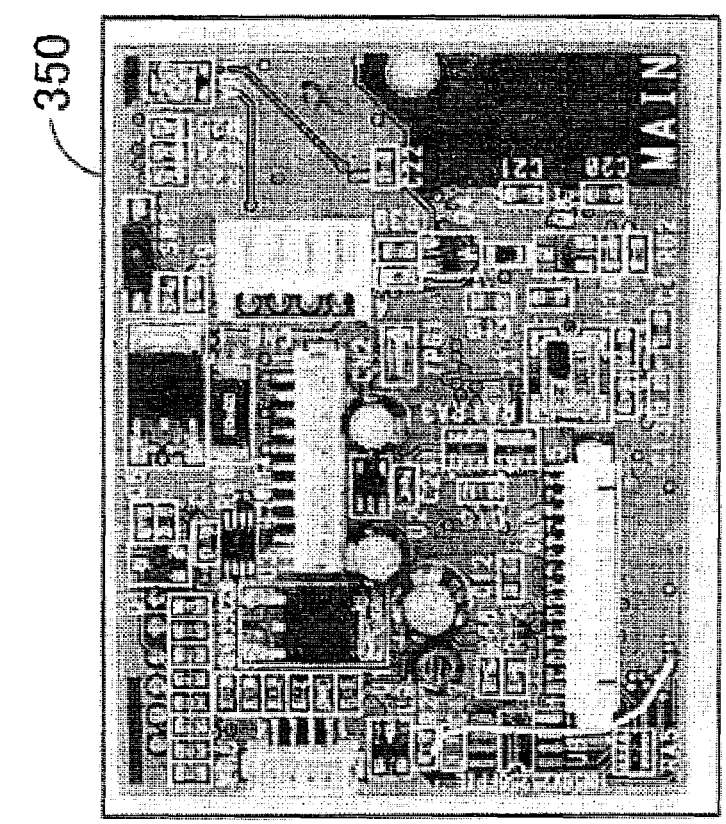
Figure 11C:
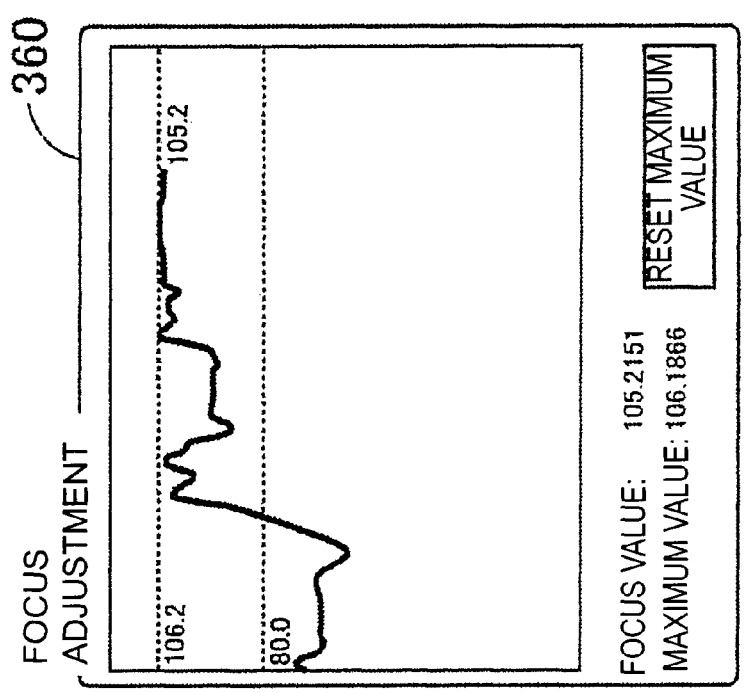

Next, a usage example of the focus adjustment screen 302 according to the present embodiment is described. FIGS. 11A to 11C are diagrams each showing an example of the focus adjustment using the focus adjustment screen 302 shown in FIG. 9. In each of FIGS. 11A to 11C, the focus value display window 360 and the image display window 350 in a certain state of the focus adjustment screen 302 are displayed in association with each other.

In FIG. 11A, an example of a state where the image is not in focus is shown. In this case, the focus value indication 3601 of the focus value display window 360 is found to indicate a relatively low value. As a result, in the image display window 350, the "blurred" input image in whole is displayed.

On the other hand, in FIG. 11B, an example of a state during the focus adjustment by the user is shown. In this case, the focus value indication 3601 of the focus value display window 360 is found to go up as time passes. In the example shown in FIG. 11B, a case where the focus is adjusted by slowly turning the focus ring of the imaging apparatus 8, thereby obtaining the maximum focus value at a certain time point, and then, the focus value again deteriorates is shown. This is what is called a case where an optimal focus position is passed. Even in this case, since in the focus value display window 360 according to the present embodiment, the maximum focus value is left as a history, the user can perform fine adjustment of the focus of the imaging apparatus 8 with this maximum focus value used as a target.

As a result, the input image in optimal focus to the subject as shown in FIG. 11C can be obtained. In the focus value display window 360 shown in FIG. 11C, the value of the focus value indication 3601 almost coincides with the maximum focus value. In this state, the image display window 350, the sharply-defined input image is displayed.

In this manner, on the focus adjustment screen 302, the maximum focus value and the input image acquired from the imaging apparatus 8 are displayed alongside, and by referring to this screen, the user can check the input image in the optimally focused state to the subject.

(c. Control Structure)

Next, a control structure to provide the focus adjustment screen 302 is described.

Figure 12:
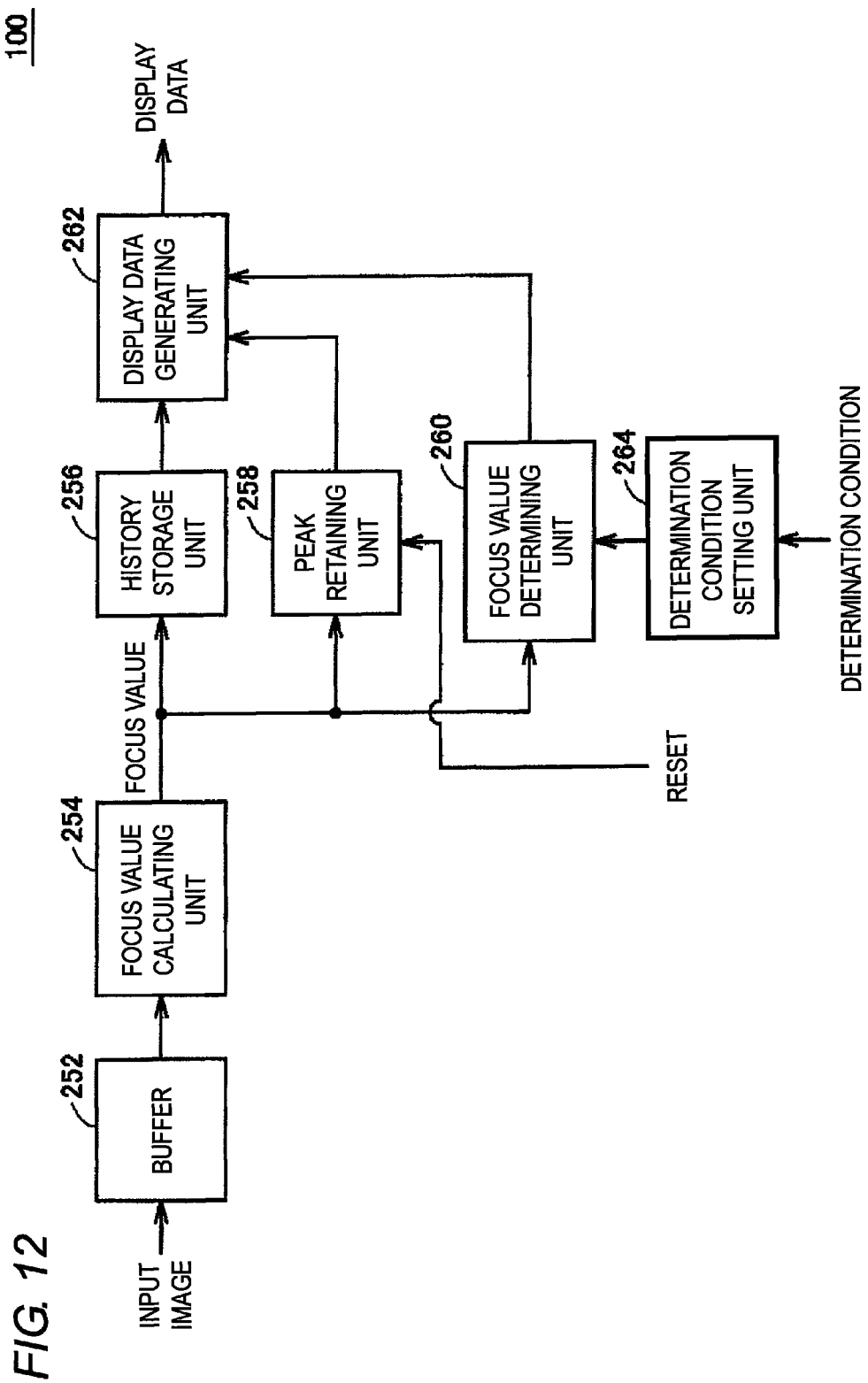
FIG. 12 is a block diagram showing a control structure to provide the focus adjustment screen according to the embodiment of the present invention.

FIG. 12 is a block diagram showing the control structure to provide the focus adjustment screen 302 according to the embodiment of the present invention. Respective blocks shown in FIG. 12 are provided by the CPU 110 developing the program (codes) stored in the hard disk 114 to the main memory 112 to execute. The program stored in the hard disk 114 may include a plurality of modules corresponding to the blocks shown in FIG. 12. Alternatively, a part or the whole of the control structure shown in FIG. 12 may be implemented by dedicated hardware and/or wiring circuitry.

Referring to FIG. 12, the image processing apparatus 100 includes, as the control structure, a buffer 252, a focus value calculating unit 254, a history storage unit 256, a peak retaining unit 258, a focus value determining unit 260, a display data generating unit 262, and a determination condition setting unit 264.

The buffer 252 temporarily accumulates the input image obtained by the imaging of the imaging apparatus 8. That is, the buffer 252 takes in the input image acquired by the imaging apparatus 8. This input image has a data structure in which the respective pixels are defined by the R density value, the G density value, and the B density value, and the buffer 252 receives access from the focus value calculating unit 254.

The focus value calculating unit 254 calculates the focus value of the input image accumulated in the buffer 252. That is, the focus value calculating unit 254 calculates the index value for evaluating the imaging state in the input image. More specifically, the focus value calculating unit 254 calculates the average value of the density values of each of the colors of the pixels included in the input image, and a square average value thereof, and then calculates the focus value in accordance with the above equation (5). The focus value calculating unit 254 sequentially outputs the calculated focus value to the history storage unit 256, the peak retaining unit 258, and the focus value determining unit 260.

The history storage unit 256 sequentially stores the focus value received from the focus value calculating unit 254. The history storage unit 256 outputs, to the display data generating unit 262, information indicating temporal change of the focus value from the latest focus value to the focus value a predetermined period before.

The peak retaining unit 258 retains the maximum value of the focus value outputted from the focus value calculating unit 254. More specifically, the peak retaining unit 258 compares a certain maximum focus value (an initial value) with the focus value outputted from the focus value calculating unit 254, and when the focus value outputted from the focus value calculating unit 254 exhibits a higher value, the focus value of interest is employed as the new maximum focus value. The comparison and update processing is sequentially repeated, thereby retaining the highest focus value (maximum focus value) of the past focus values. That is, the peak retaining unit 258 stores the maximum value of the focus values (index values) respectively calculated for the plurality of input images sequentially taken in by the buffer 252.

Furthermore, the peak retaining unit 258 outputs the retained maximum focus value to the display data generating unit 262. Moreover, the peak retaining unit 258 resets (initializes) the retained maximum focus value in response to a reset instruction from the user. That is, the peak retaining unit 258 is configured to reset the stored maximum focus value in response to the user operation.

The focus value determining unit 260 determines whether or not the focus value satisfies the preset determination condition (see the determination condition setting window 380 in FIG. 9), every time the focus value of the input image is received from the focus value calculating unit 254. The focus value determining unit 260 outputs the determination result (OK state or NG state) to the display data generating unit 262. That is, the focus value determining unit 260 determines whether or not the focus value (index value) calculated latest satisfies the determination condition.

The determination condition setting unit 264 sets the determination condition set by the user (see the determination condition setting window 380 of FIG. 9) for the focus value determining unit 260. That is, the determination condition setting unit 264 receives the determination condition concerning the focus value (index value).

The display data generating unit 262 generates the display data for displaying the focus adjustment screen 302 shown in FIG. 9. More specifically, the display data generating unit 262 dynamically generates the display contents of the focus value display window 360 based on the information indicating the temporal change of the focus value received from the history storage unit 256. Furthermore, the display data generating unit 262 determines the display aspect, based on the determination result received from the focus value determining unit 260. That is, the display data generating unit 262 changes the output aspect in accordance with the determination result by the focus value determining unit 260.

Moreover, the display data generating unit 262 displays the maximum focus value from the peak retaining unit 258 in the focus value display window 360, That is, the display data generating unit 262 outputs the maximum focus value and the focus value (index value) calculated latest.

Furthermore, the display data generating unit 262 also generates the data for displaying the input image acquired from the imaging apparatus 8, and the data for providing the user interface to set the determination condition concerning the focus value.

(d. Processing Procedure)

Next, a processing procedure concerning the focus adjustment is described.

Figure 13:
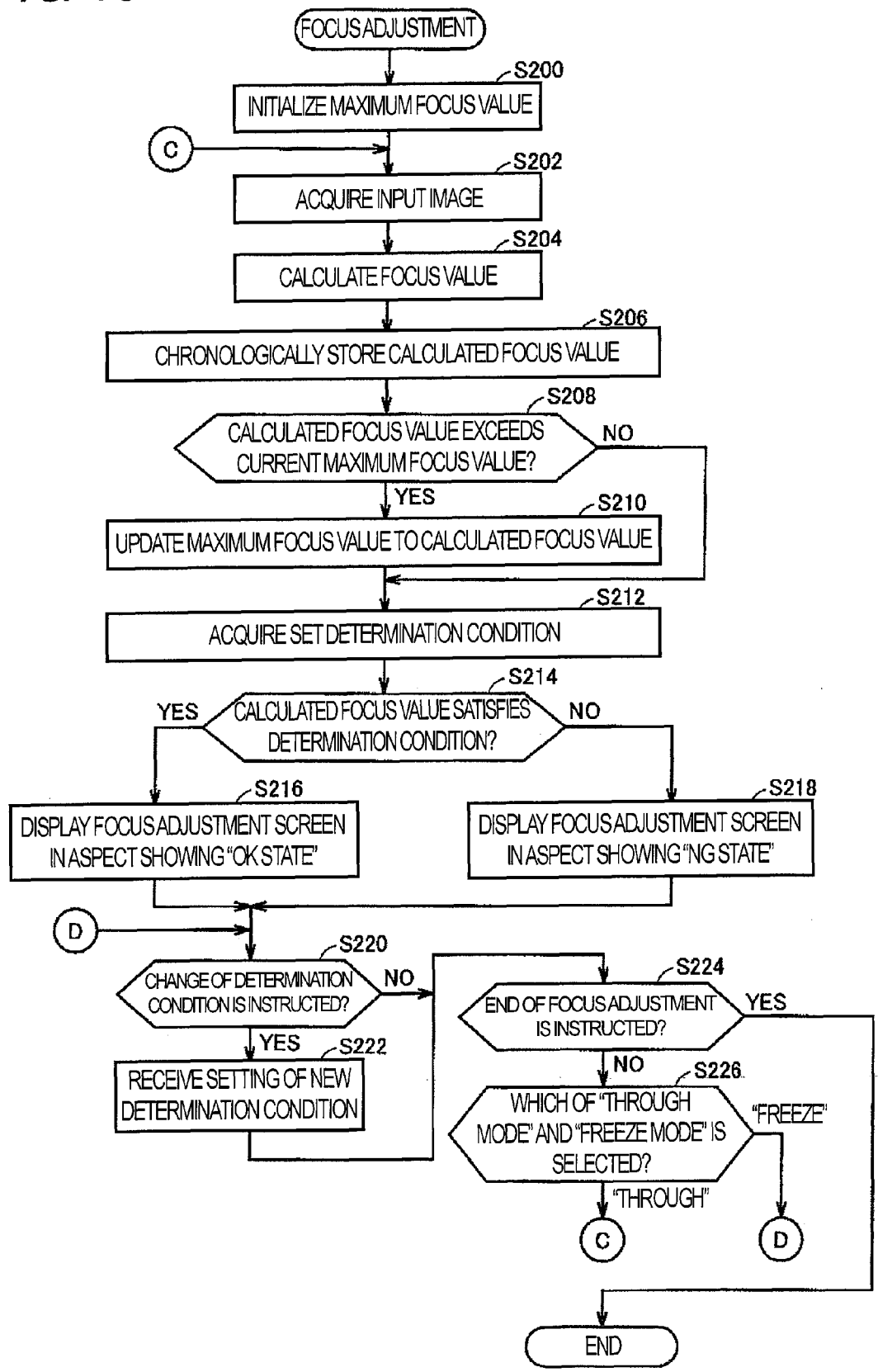
FIG. 13 is a flowchart showing a processing procedure concerning the focus adjustment according to the embodiment of the present invention.

FIG. 13 is a flowchart showing the processing procedure concerning the focus adjustment according to the embodiment of the present invention. The processing shown in FIG. 13 is started by the user performing a predetermined operation in the adjustment mode.

Referring to FIG. 13, first, the image processing apparatus 100 (the CPU 110) sets an initial value to the maximum focus value (step S200).

The imaging apparatus 8 performs imaging to thereby acquire the input image (step S202). Subsequently, the image processing apparatus 100 (the CPU 110) calculates the focus value, based on the input image (step S204). The image processing apparatus 100 (the CPU 110) sequentially stores the calculated focus value (step S206). Furthermore, the image processing apparatus 100 (the CPU 110) determines whether or not the calculated focus value exceeds the current maximum focus value (step S208).

If the calculated focus value exceeds the current maximum focus value (if YES in step S208), the image processing apparatus 100 (the CPU 110) updates the maximum focus value to the calculated focus value (step S210). The processing advances to step S212.

If the calculated focus value does not exceed the current maximum focus value (if NO in step S208), the image processing apparatus 100 (the CPU 110) acquires the set determination condition (step S212), and determines whether or not the calculated focus value satisfies the acquired determination condition (step S214).

If the determination condition is satisfied (if YES in step S214), the image processing apparatus 100 (the CPU 110) displays, on the display 102, the focus adjustment screen 302 including the focus value indication 3601 indicating the temporal change of the focus value, in the aspect showing the "OK state" (step S216).

In contrast, if the determination condition is not satisfied (if NO in step S214), the image processing apparatus 100 (the CPU 110) displays, on the display 102, the focus adjustment screen 302 including the focus value indication 3601 indicating the temporal change of the focus value, in the aspect showing the "NG state" (step S218).

Thereafter, the image processing apparatus 100 (the CPU 110) determines whether or not change of the determination condition is instructed (step S220). If the change of the determination condition is instructed (if YES in step S220), the image processing apparatus 100 (the CPU 110) receives the setting of the new determination condition from the user (step S222). The processing advances to step S224.

If the change of the determination condition is not instructed (if NO in step S220), the image processing apparatus 100 (the CPU 110) determines whether or not end of the focus adjustment is instructed (step S224). If the end of the focus adjustment is instructed (if YES in step S224), then the processing ends.

In contrast, if the end of the focus adjustment is not instructed (if NO in step S224), the image processing apparatus 100 (the CPU 110) determines which of the "through mode" and the "freeze mode" is selected (step S226).

If the "through mode" is selected ("through" in step S226), the processing in step S202 and later is repeated. On the other hand, if the "freeze mode" is selected ("freeze" in step S226), the processing in step S220 and later is repeated. That is, if the freeze mode is selected, the processing for taking in a new input image and the calculation processing of the focus value are ceased.

<Actions and Effects>

According to the image processing apparatus according to the present embodiment, by referring to the luminance adjustment screen 300 and/or the focus adjustment screen 302, the user can adjust the diaphragm amount and/or the focus in the imaging apparatus 8 while evaluating the temporal change of the effective luminance value and/or the focus value, which are the index values for evaluating the imaging state in the input image. This allows the user to perform optimal imaging setting for the imaging apparatus 8.

The embodiment disclosed herein should be considered to be not limitative but illustrative in all points. The scope of the present invention is defined not by the above description but by the scope of the claims, and it is intended that all modifications within the scope of the claims, and equivalent meanings and a range be included.

What is claimed is:

1. An image processing apparatus connected to a display apparatus and an imaging apparatus configured to change an imaging setting, the imaging processing apparatus comprising:
   a processor configured to execute program codes for controlling the image processing apparatus to function as:
   an input unit configured to take in an input image of an object in a production line acquired by the imaging apparatus;
   a calculation unit configured to calculate an effective luminance value which is according to a number of pixels having a luminance within a preset effective luminance range included in the input image; and
   an output unit configured to output a history of the temporal change of the effective luminance value, the history includes the effective luminance value calculated latest and the effective luminance value calculated before the effective luminance value calculated latest,
   wherein
   the output unit is configured to display a graph of the effective luminance value on a time axis as the history of the temporal change of the effective luminance value,
   wherein the effective luminance value is a percentage of the number of the pixels having the luminance within the preset effective luminance range defined by a lower limit value and an upper limit value to the total number of pixels included in the input image,
   wherein the calculation unit is configured to calculate a percentage of the number of pixels having a luminance which is higher or lower than the higher limit value or the lower limit value, respectively, to the total number of pixels included in the input image as a first ineffective luminance value or a second ineffective luminance value, respectively, and
   the output unit is configured to display a history of a temporal change of the first ineffective luminance value or the second ineffective luminance value, respectively.

2. The image processing apparatus according to claim 1, the image processing apparatus being controlled by the program codes to function as a receiving unit configured to receive the lower limit value and the upper limit value.

3. The image processing apparatus according to claim 2, wherein
   the calculation unit is configured to further calculate an ineffective luminance value which is a percentage of the number of the pixels having a luminance without the effective luminance range to the total number of pixels included in the input image.

4. The image processing apparatus according to claim 1, wherein the calculation unit is configured to calculate the percentage of the number of the pixels having the luminance which is higher than the upper limit value to the total number of pixels included in the unit image as the first ineffective luminance value, and the output unit is configured to display the history of the temporal change of the first ineffective luminance value, and
   the calculation unit is configured to calculate the percentage of the number of the pixels having the luminance which is lower than the lower limit value to the total number of pixels included in the input image as the second ineffective luminance value, and
   the output unit is configured to display the history of the temporal change of the second ineffective luminance value.

5. An image processing method in an image processing apparatus connected to a display apparatus and an imaging apparatus configured to change an imaging setting, the method comprising:
   an input step of taking in an input image of an object in a production line acquired by the imaging apparatus;
   a calculation step of calculating an effective luminance value which is according to a number of pixels having a luminance within a preset effective luminance range included in the input image, wherein the effective luminance value is a percentage of the number of the pixels having the luminance within the preset effective luminance range defined by a lower limit value and an upper limit value to the total number of pixels included in the input image;
   a calculation step of calculating a percentage of the number of the pixels having the luminance which is higher or lower than the higher limit value or the lower limit value, respectively, to the total number of pixels included in the input image as a first ineffective luminance value or a second ineffective luminance value, respectively; and
   an output step of outputting a history of the temporal change of the effective luminance value, the history includes the effective luminance value calculated latest and the effective luminance value calculated before the effective luminance value calculated latest,
   wherein
   the output step comprises:
   displaying a graph of the effective luminance value on a time axis as the history of the temporal change of the effective luminance value, and
   displaying a history of a temporal change of the first ineffective luminance value or the second ineffective luminance value, respectively.

6. A non-transitory computer-readable storage medium in which an image processing program to be executed in a computer connected to a display apparatus and an imaging apparatus configured to change an imaging setting is stored,
  wherein the imaging processing program causes the computer to function as:
    an input unit configured to take in an input image of an object in a production line acquired by the imaging apparatus;
    a calculation unit configured to calculate an effective luminance value which is according to a number of pixels having a luminance within a preset effective luminance range included in the input image; and
    an output unit configured to output a history of the temporal change of the effective luminance value, the history includes the effective luminance value calculated latest and the effective luminance value calculated before the effective luminance value calculated latest,
  wherein
    the output unit is configured to display a graph of the effective luminance value on a time axis as the history of the temporal change of the effective luminance value,
  wherein the effective luminance value is a percentage of the number of the pixels having the luminance within the preset effective luminance range defined by a lower limit value and an upper limit value to the total number of pixels included in the input image,
  wherein the calculation unit is configured to calculate a percentage of the number of the pixels having the luminance which is higher or lower than the higher limit value or the lower limit value, respectively, to the total number of pixels included in the input image as a first ineffective luminance value or a second ineffective luminance value, respectively, and
    the output unit is configured to display a history of a temporal change of the first ineffective luminance value or the second ineffective luminance value, respectively.

7. The image processing apparatus according to claim 1, wherein the calculation unit is configured to further calculate an ineffective luminance value which is a percentage of the number of the pixels having a luminance without the effective luminance range to the total number of pixels included in the input image.

8. The image processing apparatus according to claim 2, wherein the calculation unit is configured to calculate the percentage of the number of the pixels having the luminance which is higher than the upper limit value to the total number of pixels included in the input image as the first ineffective luminance value, and the output unit is configured to display the history of the temporal change of the first ineffective luminance value, and
  the calculation unit is configured to calculate the percentage of the number of the pixels having the luminance which is lower than the lower limit value to the total number of pixels included in the input image as the second ineffective luminance value, and
  the output unit is configured to display the history of a temporal change of the second ineffective luminance value.

9. The image processing apparatus according to claim 3, wherein the calculation unit is configured to calculate the percentage of the number of the pixels having the luminance which is higher than the upper limit value to the total number of pixels included in the input image as the first ineffective luminance value, and the output unit is configured to display the history of the temporal change of the first ineffective luminance value, and
  the calculation unit is configured to calculate the percentage of the number of the pixels having the luminance which is lower than the lower limit value to the total number of pixels included in the input image as the second ineffective luminance value, and
  the output unit is configured to display the history of a temporal change of the second ineffective luminance value.

10. The image processing apparatus according to claim 1, the image processing apparatus being controlled by the program codes to function as:
  a determination condition input unit configured to receive a determination condition concerning the effective luminance value; and
  a determination unit configured to determine whether or not the effective luminance value calculated latest satisfies the determination condition, wherein
  the output unit is configured to switch an output aspect in accordance with a determination result by the determination unit.

11. The image processing apparatus according to claim 2, the image processing apparatus being controlled by the program codes to function as:
  a determination condition input unit configured to receive a determination condition concerning the effective luminance value; and
  a determination unit configured to determine whether or not the effective luminance value calculated latest satisfies the determination condition, wherein
  the output unit is configured to switch an output aspect in accordance with a determination result by the determination unit.

12. The image processing apparatus according to claim 3, the image processing apparatus being controlled by the program codes to function as:
  a determination condition input unit configured to receive a determination condition concerning the effective luminance value; and
  a determination unit configured to determine whether or not the effective luminance value calculated latest satisfies the determination condition, wherein
  the output unit is configured to switch an output aspect in accordance with a determination result by the determination unit.

13. The image processing apparatus according to claim 4, the image processing apparatus being controlled by the program codes to function as:
  a determination condition input unit configured to receive a determination condition concerning the effective luminance value; and
  a determination unit configured to determine whether or not the effective luminance value calculated latest satisfies the determination condition, wherein
  the output unit is configured to switch an output aspect in accordance with a determination result by the determination unit.

14. The image processing apparatus according to claim 7, wherein the calculation unit is configured to calculate the percentage of the number of the pixels having the luminance which is higher than the upper limit value to the total number of pixels included in the input image as the first ineffective luminance value, and
  the output unit is configured to display the history of the temporal change of the first ineffective luminance value, and
  the calculation unit is configured to calculate a percentage of the number of the pixels having a luminance which is lower than the lower limit value to the total number of pixels included in the input image as a second ineffective luminance value, and the output unit is configured to display a history of a temporal change of the second ineffective luminance value.

15. The image processing apparatus according to claim 7, the image processing apparatus being controlled by the program codes to function as:

a determination condition input unit configured to receive a determination condition concerning the effective luminance value; and a determination unit configured to determine whether or not the effective luminance value calculated latest satisfies the determination condition, wherein the output unit is configured to switch an output aspect in accordance with a determination result by the determination unit.

* * * * *